US008614200B2

(12) United States Patent
Painter et al.

(10) Patent No.: US 8,614,200 B2
(45) Date of Patent: Dec. 24, 2013

(54) COMPOUNDS, COMPOSITIONS AND METHODS FOR TREATING OCULAR CONDITIONS

(75) Inventors: George R. Painter, Chapel Hill, NC (US); Merrick R. Almond, Apex, NC (US)

(73) Assignee: Chimerix, Inc., Durham, NC (US)

( * ) Notice: Subject to any disclaimer, the term of this patent is extended or adjusted under 35 U.S.C. 154(b) by 1 day.

(21) Appl. No.: 13/386,604

(22) PCT Filed: Jul. 21, 2010

(86) PCT No.: PCT/US2010/042749
§ 371 (c)(1),
(2), (4) Date: Mar. 16, 2012

(87) PCT Pub. No.: WO2011/011519
PCT Pub. Date: Jan. 27, 2011

(65) Prior Publication Data
US 2012/0165295 A1    Jun. 28, 2012

Related U.S. Application Data

(60) Provisional application No. 61/227,148, filed on Jul. 21, 2009, provisional application No. 61/332,305, filed on May 7, 2010.

(51) Int. Cl.
*A61K 31/675* (2006.01)
(52) U.S. Cl.
USPC .......................................................... 514/86
(58) Field of Classification Search
USPC .......................................................... 514/86
See application file for complete search history.

(56) References Cited

U.S. PATENT DOCUMENTS

| | | |
|---|---|---|
| 1,944,530 A | 1/1934 | Schonburg |
| 3,422,021 A | 1/1969 | Roy |
| 3,468,935 A | 9/1969 | Peck |
| 4,327,039 A | 4/1982 | Blum et al. |
| 4,444,766 A | 4/1984 | Bosies et al. |
| 4,562,179 A | 12/1985 | Teraji et al. |
| 4,619,794 A | 10/1986 | Hauser |
| 4,705,651 A | 11/1987 | Staibano |
| 4,870,063 A | 9/1989 | Binderup et al. |
| 4,927,814 A | 5/1990 | Gall et al. |
| 5,043,437 A | 8/1991 | Khorlin et al. |
| 5,047,533 A | 9/1991 | Reist et al. |
| 5,142,051 A | 8/1992 | Holy et al. |
| 5,183,815 A | 2/1993 | Saari et al. |
| 5,194,654 A | 3/1993 | Hostetler et al. |
| 5,196,409 A | 3/1993 | Breuer et al. |
| 5,223,263 A | 6/1993 | Hostetler et al. |
| 5,247,085 A | 9/1993 | Harnden et al. |
| 5,300,671 A | 4/1994 | Tognella et al. |
| 5,300,687 A | 4/1994 | Schwender et al. |
| 5,312,954 A | 5/1994 | Breuer et al. |
| 5,395,826 A | 3/1995 | Naumann et al. |
| 5,411,947 A | 5/1995 | Hostetler et al. |
| 5,428,181 A | 6/1995 | Sugioka et al. |
| 5,442,101 A | 8/1995 | Hanhijarvi et al. |
| 5,463,092 A | 10/1995 | Hostetler et al. |
| 5,476,938 A | 12/1995 | Vemishetti et al. |
| 5,484,809 A | 1/1996 | Hostetler et al. |
| 5,484,911 A | 1/1996 | Hong et al. |
| 5,512,671 A | 4/1996 | Piantadosi et al. |
| 5,532,226 A | 7/1996 | Demarest et al. |
| 5,591,852 A | 1/1997 | Vemishetti et al. |
| 5,614,548 A | 3/1997 | Piantadosi et al. |
| 5,627,185 A | 5/1997 | Gosselin et al. |
| 5,650,510 A | 7/1997 | Webb, II et al. |
| 5,656,745 A | 8/1997 | Bischofberger et al. |
| 5,663,159 A | 9/1997 | Starrett, Jr. et al. |
| 5,672,697 A | 9/1997 | Buhr et al. |
| 5,696,277 A | 12/1997 | Hostetler et al. |
| 5,717,095 A | 2/1998 | Arimilli et al. |
| 5,744,461 A | 4/1998 | Hostetler et al. |
| 5,744,592 A | 4/1998 | Hostetler et al. |
| 5,756,711 A | 5/1998 | Zilch et al. |

(Continued)

FOREIGN PATENT DOCUMENTS

| | | |
|---|---|---|
| CS | 220713 B1 | 4/1983 |
| EP | 0186405 A2 | 7/1986 |
| EP | 0253412 A2 | 1/1988 |
| EP | 0632048 A1 | 1/1995 |
| EP | 0753523 A1 | 1/1997 |
| EP | 0897709 A1 | 2/1999 |
| EP | 1438962 A1 | 7/2004 |
| EP | 1914237 A2 | 4/2008 |
| GB | 1280788 A | 7/1972 |
| JP | 61152694 A | 7/1986 |

(Continued)

OTHER PUBLICATIONS

"Creating Orally Available Medicines from Bioactive Molecules." Presentation at Big 2004 Annual International Convention. (Jun. 7, 2004).
Aldern et al. "Increased Antiviral Activity of 1-*O*-Hexadecyloxypropyl-[2-14C]Cidofovir in MRC-5 Human Lung Fibroblasts is Explained by Unique Cellular Uptake and Metabolism." *Mol. Pharmacol.* 63.3(2003):678-681.
Andrei et al. "Activities of Various Compounds against Murine and Primate Polyomaviruses." *Antimicrob. Agents Chemother.* 41.3(1997):587-593.

(Continued)

*Primary Examiner* — Raymond Henley, III
(74) *Attorney, Agent, or Firm* — Mintz Levin Cohn Ferris Glovsky and Popeo, P.C.; Ivor R. Elrifi; Heidi A. Erlacher

(57) ABSTRACT

The present invention provides methods of treating viral infection of the eye or posterior ocular condition including administering a pharmaceutical composition comprising a compound described in the present application. In some embodiments, the pharmaceutical composition is topically administered. In another embodiment, the pharmaceutical composition is orally administered or intraocularly administered.

20 Claims, No Drawings

(56) References Cited

U.S. PATENT DOCUMENTS

| | | | |
|---|---|---|---|
| 5,760,013 A | 6/1998 | Hwu et al. |
| 5,770,584 A | 6/1998 | Kucera et al. |
| 5,780,617 A | 7/1998 | van den Bosch et al. |
| 5,792,756 A | 8/1998 | Starrett, Jr. et al. |
| 5,798,340 A | 8/1998 | Bischofberger et al. |
| 5,817,638 A | 10/1998 | Hostetler |
| 5,827,831 A | 10/1998 | Hostetler et al. |
| 5,840,716 A | 11/1998 | Ubasawa et al. |
| 5,854,228 A | 12/1998 | Webb, II et al. |
| 5,856,314 A | 1/1999 | Kaas et al. |
| 5,869,468 A | 2/1999 | Freeman |
| 5,877,166 A | 3/1999 | Reist et al. |
| 5,885,973 A | 3/1999 | Papapoulos et al. |
| 5,886,179 A | 3/1999 | Arimilli et al. |
| 5,922,695 A | 7/1999 | Arimilli et al. |
| 5,922,696 A | 7/1999 | Casara et al. |
| 5,962,437 A | 10/1999 | Kucera et al. |
| 5,977,061 A | 11/1999 | Holy et al. |
| 5,977,089 A | 11/1999 | Arimilli et al. |
| 6,002,029 A | 12/1999 | Hostetler et al. |
| 6,030,960 A | 2/2000 | Morris-Natschke et al. |
| 6,043,230 A | 3/2000 | Arimilli et al. |
| 6,069,249 A | 5/2000 | Arimilli et al. |
| 6,194,388 B1 | 2/2001 | Krieg et al. |
| 6,207,646 B1 | 3/2001 | Krieg et al. |
| 6,218,371 B1 | 4/2001 | Krieg et al. |
| 6,225,292 B1 | 5/2001 | Raz et al. |
| 6,239,116 B1 | 5/2001 | Krieg et al. |
| 6,252,060 B1 | 6/2001 | Hostetler |
| 6,448,392 B1 | 9/2002 | Hostetler et al. |
| 6,562,798 B1 | 5/2003 | Schwartz |
| 6,589,940 B1 | 7/2003 | Raz et al. |
| 6,605,602 B1 | 8/2003 | Vats |
| 6,635,472 B1 | 10/2003 | Lauermann |
| RE38,333 E | 11/2003 | Arimilli et al. |
| 6,670,341 B1 | 12/2003 | Kucera et al. |
| 6,716,825 B2 | 4/2004 | Hostetler et al. |
| 6,818,629 B2 | 11/2004 | Peterson et al. |
| 7,026,469 B2 | 4/2006 | Kucera et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,288,265 B1 | 10/2007 | Rolf |
| 7,390,791 B2 | 6/2008 | Becker et al. |
| 7,452,898 B2 | 11/2008 | Hostetler et al. |
| 7,652,001 B2 | 1/2010 | Hostetler et al. |
| 7,749,983 B2 | 7/2010 | Hostetler et al. |
| 7,790,703 B2 | 9/2010 | Hostetler et al. |
| 2003/0211072 A1 | 11/2003 | Carreno-Gomez et al. |
| 2004/0019232 A1 | 1/2004 | Hostetler et al. |
| 2004/0022873 A1 | 2/2004 | Guilford et al. |
| 2004/0071757 A1 | 4/2004 | Rolf |
| 2004/0161398 A1 | 8/2004 | Kucera et al. |
| 2004/0224917 A1 | 11/2004 | Dahl et al. |
| 2004/0259845 A1 | 12/2004 | Kucera et al. |
| 2005/0187192 A1 | 8/2005 | Fleming et al. |
| 2005/0261237 A1 | 11/2005 | Boojamra et al. |
| 2006/0128692 A1 | 6/2006 | Chen et al. |
| 2006/0263355 A1 | 11/2006 | Quan et al. |
| 2007/0003516 A1 | 1/2007 | Almond et al. |
| 2007/0003608 A1 | 1/2007 | Almond et al. |
| 2007/0026056 A1 | 2/2007 | Rolf |
| 2008/0009462 A1 | 1/2008 | Hostetler et al. |
| 2008/0020018 A1 | 1/2008 | Moodley et al. |
| 2008/0161324 A1 | 7/2008 | Johansen et al. |
| 2009/0017448 A1 | 1/2009 | Toth et al. |
| 2009/0087451 A1 | 4/2009 | Buller |
| 2009/0111774 A1 | 4/2009 | Tokars et al. |
| 2010/0173870 A1 | 7/2010 | Hostetler et al. |

FOREIGN PATENT DOCUMENTS

| | | |
|---|---|---|
| JP | 10029998 A | 2/1998 |
| WO | WO-9105558 A1 | 5/1991 |
| WO | WO-9109602 A2 | 7/1991 |
| WO | WO-9520980 A1 | 8/1995 |
| WO | WO-9602555 A1 | 2/1996 |
| WO | WO-9640088 A1 | 12/1996 |
| WO | WO-9728259 A1 | 8/1997 |
| WO | WO-9816247 A1 | 4/1998 |
| WO | WO-9818810 A1 | 5/1998 |
| WO | WO-9838202 A1 | 9/1998 |
| WO | WO-9840100 A1 | 9/1998 |
| WO | WO-9852581 A9 | 11/1998 |
| WO | WO-9908685 A1 | 2/1999 |
| WO | WO-9855495 B1 | 7/1999 |
| WO | WO-0004032 A1 | 1/2000 |
| WO | WO-9951259 A3 | 1/2000 |
| WO | WO-0006588 B1 | 4/2000 |
| WO | WO-0037477 A1 | 6/2000 |
| WO | WO-0112223 A3 | 9/2001 |
| WO | WO-0021556 A9 | 10/2001 |
| WO | WO-0122990 A3 | 10/2001 |
| WO | WO-0139724 A3 | 10/2001 |
| WO | WO-03049746 A2 | 6/2003 |
| WO | WO-2004062600 A2 | 7/2004 |
| WO | WO-2004112718 A3 | 4/2005 |
| WO | WO-2005087788 A2 | 9/2005 |
| WO | WO-2005121378 A2 | 12/2005 |
| WO | WO-2006066074 A2 | 6/2006 |
| WO | WO-2006076015 A2 | 7/2006 |
| WO | WO-2006110655 A2 | 10/2006 |
| WO | WO-2006110656 A2 | 10/2006 |
| WO | WO-0122972 A9 | 12/2006 |
| WO | WO-2006130217 A2 | 12/2006 |
| WO | WO-2007130783 A2 | 11/2007 |
| WO | WO-2008033466 A2 | 3/2008 |
| WO | WO-2008118013 A2 | 10/2008 |
| WO | WO-2008133966 A1 | 11/2008 |
| WO | WO-2008133982 A2 | 11/2008 |
| WO | WO-2008144743 A1 | 11/2008 |
| WO | WO-2011011519 A1 | 1/2011 |
| WO | WO-2011017253 A1 | 2/2011 |
| WO | WO-2011053812 A1 | 5/2011 |

OTHER PUBLICATIONS

Annaert et al. "In Vitro, Ex Vivo, and In Situ Intestinal Absorption Characteristics of the Antiviral Ester Prodrug Adefovir Dipivoxil." *J. Pharm. Sci.* 89.8(2000):1054-1062.

Balzarini et al. "Antiretrovirus Activity of a Novel Class of Acyclic Pyrimidine Nucleoside Phosphonates." *Antimicrob. Agents Chemother.* 45.7(2002):2185-2193.

Bartlett et al. "Phase I Trial of Doxorubicin with Cyclosporine as a Modulator of Multidrug Resistance." *J. Clin. Oncol.* 12.4(1994):835-842.

Beadle et al. "Alkoxyalkyl Esters of Cidofovir and Cyclic Cidofovir Exhibit Multiple-Log Enhancement of Antiviral Activity Against Cytomegalovirus and Herpes Virus Replication in Vitro." *Antimicrob Agents Chemother.* 46.8(2002):2381-2386.

Bell et al. "Antibodies Against the Extracellular Enveloped Virus B5R Proteins are Mainly Responsible for the EEV Neutralizing Capacity of Vaccinia Immune Globulin." *J. Virol.* 325.2(2004):425-431.

Bidanset et al. "Oral Activity of Ether Lipid Ester Prodrugs of Cidofovir against Experimental Human Cytomegalovirus Infection." *J. Infect. Dis.* 190.3(2004):499-503.

Biron. "Antiviral Drugs for Cytomegalovirus Diseases." *Antiviral Res.* 71(2006):154-163.

Blasco et al. "Extracellular Vaccinia Virus Formation and Cell-to-Cell Virus Transmission are Prevented by Deletion of the Gene Encoding the 37,000-Dalton Outer Envelope Protein." *J. Virol.* 65.11(1991):5910-5920.

Bray et al. "Antiviral Prophylaxis of Smallpox." *J. Antimicrob. Chemother.* 54.1(2004):1-5.

Bray. "Pathogenesis and Potential Antiviral Therapy of Complications of Smallpox Vaccination." *Antiviral Res.* 58.2(2003):101-114.

(56) References Cited

OTHER PUBLICATIONS

Buller et al. "Efficacy of Oral Active Ether Lipid Analogs of Cidofovir in a Lethal Mousepox Model." *Virol*. 318.2(2004):474-481.

Buller et al. "Efficacy of Smallpox Vaccination in the Presence of Antiviral Drugs, Cidofovir, and Hexadecyoxypropylcidofovir." *Antiviral Res*. 65.3(2005):A80. (Abstract #72).

Ciesla et al. "Esterification of Cidofovir with Alkoxyalkanols Increases Oral Bioavailability and Diminishes Drug Accumulation in Kidney." *Antiviral Res*. 59.3(2003):163-171.

Connelly et al. "Mechanism of Uptake of the Phosphonate Analog (S)-1-(3-hydroxy-2-phosphonylnnethoxy-propyl)Cytosine (HPMPC) in Vero Cells." *Biochem. Pharma*. 46.6(1993):1053-1057.

Dal Pozzo et al. "In Vitro Evaluation of the Anti-offVirus Activity of Alkoxyalkyl Esters of CDV, cCDV and (S)-HPMPA." *Antiviral Res*. 75(2007):52-57.

De Clercq et al. "Therapeutic Potential of Nucleoside/Nucleotide Analogues Against Poxvirus Infections." *Rev. Med. Virol*. 14.5(2004):289-300.

De Clercq. "Antiviral Drugs in Current Clinical Use." *J. Virol*. 30.2(2004):115-133.

De Clercq. "Clinical Potential of the Acyclic Nucleoside Phosphonates Cidofovir, Adefovir, and Tenofovir in Treatment of DNA Virus and Retrovirus Infections." *Clin. Microbiol. Rev*. 16.4(2003):569-596.

De Clercq. "The Acyclic Nucleoside Phosphonates from Inception to Clinical Use: Historical Perspective." *Antiviral Res*. 75(2007):1-13.

De Clercq. "Vaccinia Virus Inhibitors as a Paradigm for the Chemotherapy of Poxvirus Infections." *Clin. Microbiol. Rev*. 14.2(2001):382-397.

Denes et al. "Main Adult Herpes Virus Infections of the CNS." *Anti-Infective Therapy*. 3.4(2005):663-678.

Fardis et al. "Case Study: Tenofovir Disoproxil Fumarate: An Oral Prodrug of Tenofovir." vol. V: *Prodrugs: Challenges and Rewards Part 1. Biotechnology, Pharmaceutical Aspects*. 5.20(2007):649-657.

Fisher et al. "Phase I Trial of Etoposide with the Cyclosporine 5DZ PSC 833, a Modulator of Multidrug Resistance (MDR)." *Proc. Am Soc. Clin. Oncol*. 12(1994):143 (Abstract #368).

Gauvry et al. "Dealkylation of Dialkyl Phosphonates with Boron Tribromide." *Synthesis*. 4(2001):553-554.

Hammond et al. "Alkylglycerol Prodrugs of Phosphonoformate are Potent In Vitro Inhibitors of Nucleoside-Resistant Human Immunodeficiency Virus Type 1 and Select for Resistance Mutations that Suppress Zidovudine Resistance." *Antimicrob. Agents Chemother*. 45.6(2001):1621-1628.

Hartline et al. "Ether Lipid-Ester Prodrugs of Acyclic Nucleoside Phosphonates: Activity Against Adenovirus Replication In Vitro." *J. Infect. Dis*. 191.3(2005):396-399.

Held et al. "Treatment of BK Virus-Associated Hemorrhagic Cystitis and Simultaneous CMV Reactivation with Cidofovir." *Bone Marrow Transplant*. 26(2000):347-350.

Hillenkamp et al. "Topical Treatment of Acute Adenoviral Keratoconjunctivitis With 0.2% Cidofovir and 1% Cyclosporine." *Arch. Ophthalmol*. 119.10(2001):1487-1491.

Hockova et al. "5-Substituted-2,4-diamino-642-(phosphonomethoxy)ethoxy]pyrimidines-Acyclic Nucleoside Phosphonate Analogues with Antiviral Activity." *J. Med. Chem*. 46.23(2003):5064-5073.

Holy et al. "6-[2-(Phosphonomethoxy)alkoxy]pyrimidines with Antiviral Activity." *J. Med. Chem*. 45.9(2002):1918-1929.

Holy et al. "Structure-Antiviral Activity Relationship in the Series of Pyrimidine and Purine N-[2(2-Phosphonomethoxy)ethyl] Nucleotide Analogues." *J. Med. Chem*. 42.12(1999):2064-2086.

Holy. "Phosphonomethoxyalkyl Analogs of Nucleotides." *Curr. Pharma Des*. 9.31(2003):2567-2592.

Holy. "Simple Method for Cleavage of Phosphonic Acid Diesters to Monoesters." *Synthesis*.4(1998):381-385.

Hostetler et al. "Enhanced Antiproliferative Effects of Alkoxyalkyl Esters of Cidofovir in Human Cervical Cancers Cells in vitro." *Mol. Cancer Ther*. 5.1(2005):156-159.

Hostetler. "Alkoxyalkyl Prodrugs of Acyclic Nucleoside Phosphonates Enhance Oral Antiviral Activity and Reduce Toxicity: Current State of the Art." *Antiviral Research*. 82.2(2009):A84-A98.

Huggins et al. "Cidofovir Treatment of Variola (Smallpox) in the Hemorrhagic Smallpox Primate Model and the IV Monkeypox Primate Model." *Antiviral Res*. 57.3(2003):A78. (Abstract #127).

Huggins et al. "Orally Active Ether Lipid Prodrugs of Cidofovir for the Treatment of Smallpox." *Antiviral Res*. 53(2002):A66. (Abstract #104).

Huggins et al. "Successful Cidofovir Treatment of Smallpox-Like Disease in Variola and Monkeypox Primate Models." *Antiviral Res*. 62.2(2004):A57-A58. (Abstract #76).

Jacobson. "Treatment of Cytomegalovirus Retinitis in Patients with the Acquired Immunodeficiency Syndrome." *Drug Ther*. 337(1997):105-114.

Jasko et al. "A New Approach to Synthesis of 5'-)-phosphonomethyl Derivatives of Nucleosides and Their Analogues." *Bioorganicheskaya Khimiya*. 20.1(1994):50-54. (English Abstract Only).

Josephson et al. "Polyomavirus-Associated Nephropathy: Update on Antiviral Strategies." *Transpl. Infect. Dis*. 8(2006):95-101.

Keith et al. "Evaluation of Nucleoside Phosphonates and Their Analogs and Prodrugs for Inhibition of Orthopoxvirus Replication." *Antimicrob Agents Chemother*. 47.7(2003):2193-2198.

Keith et al. "Inhibitory Activity of Alkoxyalkyl and Alkyl Esters of Cidofovir and Cyclic Cidofovir Against Orthopoxvirus Replication In Vitro." *Antimicrob Agents Chemother*. 48.5(2004):1869-1871.

Kern et al. "Enhanced Inhibition of Orthopoxvirus Replication In Vitro by Alkoxyalkyl Esters of Cidofovir and Cyclic Cidofovir." *Antimicrob Agents Chemother*. 46.4(2002):991-995.

Kern et al. "Oral Treatment of Murine Cytomegalovirus Infections with Ether Lipid Esters of Cidofovir." *Antimicrob Agents Chemother*. 48.9(2004):3516-3522.

Kern. "Pivotal Role of Animal Models in the Development of New Therapies for Cytomegalovirus Infections." *Antiviral Res*. 71(2006):164-171.

Kini et al. "Alkoxy Propane Prodrugs of Foscarnet: Effect of Alkyl Chain Length on In Vitro Antiviral Activity in Cells Infected with HIV-1, HSV-1 and HCMV." *Antiviral Res*. 36.1(1997):43-53.

Komori et al. "Cytochrome P-450 in Human Liver Microsomes: High-Performance Liquid Chromatographic Isolation of Three Forms and Their Characterization." *J. Biochem.(Tokyo)*. 104.6(1988):912-916.

Kornbluth et al. "Mutations in the E9L Polymerase Gene of Cidofovir-Resistant Vaccinia Virus Strain WR are Associated with the Drug Resistance Phenotype." *Antimicrob. Agents Chemother*. 50.12(2006):4038-4043.

Lebeau et al. "Activities of Alkoxyalkyl Esters of Cidofovir (CDV), Cyclic CDV, and (S)-9-(3-Hydroxy-2-Phosphonylmethoxypropyl)Adenine Against Orthopoxviruses in Cell Monolayers and in Organotypic Cultures." *Antimicrob. Agents Chemother*. 50.7(2006):2525-2529.

Lu et al. "Intraocular Properties of Hexadecyloxypropyl-Cyclic-Cidofovir in Guinea Pigs." *J. Ocul. Pharmacol. Ther*. 21.3(2005):205-209.

Lum et al. "Alteration of Etoposide Pharmacokinetics and Pharmacodynamics by Cyclosporine in a Phase I Trial to Modulate Multidrug Resistance." *J. Clin. Oncol*. 10.10(1992):1635-1642.

Lum et al. "MDR Expression in Normal Tissues." *Hematol. Oncol. Clin. No. Amer*. 9.2(1995):319-336.

Niemi et al. "Bisphosphonate Prodrugs: Synthesis and in Vitro Evaluation of Novel Acyloxyalkyl Esters of Clodronic Acid." *J. Med. Chem*. 42.24(1999):5053-5058.

Painter et al. "Biochemical and Mechanistic Basis for the Activity of Nucleoside Analogue Inhibitors of HIV Reverse Transcriptase." *Curr. Topics Med. Chem*. 4.10(2004):1035-1044.

Painter et al. "Design and Development of Oral Drugs for the Prophylaxis and Treatment of Smallpox Infection." *Trends Biotechnol*. 22.8(2004):423-427.

(56) References Cited

OTHER PUBLICATIONS

Parker et al. "Efficacy of Therapeutic Intervention with an Oral Ether-Lipid Analogue of Cidofovir (CMX001) in a Lethal Mousepox Model." *Antiviral Res.* 77.1(2008):39-49.

Portilla et al. "Progressive Multifocal Leukoencephalopathy Treated with Cidofovir in HIV-Infected Patients Receiving Highly Active Anti-Retroviral Therapy." *J. Infect.* 41(2000):182-184.

Quenelle et al. "Oral Treatment of Cowpox and Vaccinia Virus Infections in Mice with Ether Lipid Esters of Cidofovir." *Antimicrob. Agents Chemother.* 48.2(2004):404-412.

Quenelle et al. "Oral Treatment of Cowpox and Vaccinia Virus Infections in Mice with Ether Lipid Esters of Cidofovir." *Antimicrob. Agents Chemother.* 48.2(2004):404-412. Erratum in: *Antimicrob. Agents Chemother.* 48.5(2004):1919.

Quenelle et al. "Synergistic Efficacy of the Combination of ST-246 with CMX001 Against Orthopoxviruses." *Antimicrob. Agents Chemother.* 51.11(2007):4118-4127.

Quimby et al. "Tetrasodium Carbonyldiphosphonate." *J. Org. Chem.* 32.12(1967):4111-4114.

Randhawa et al. "Ether Lipids Ester Derivatives of Cidofovir Inhibit Polyomavirus BK Replication In Vitro." *Antimicrob. Agents Chemother.* 50.4(2006):1564-1566.

Remichkova et al. "Synergistic Combination Effect of Cidofovir and Idoxuridine on Vaccinia Virus Replication." *Antiviral Res.* 65.3(2005):A80-A81. (Abstract #74).

Rogers. "A General Synthesis of Phosphonic Acid Dichlorides Using Oxalyl Chloride and DMF Catalysis." *Tetrahed. Lett.* 33.49(1992):7473-7474.

Saady et al. "Direct Esterification of Phosphonic Acid Salts Using the Mitsunobu Reaction." *Synlett.* 6(1995):643-644.

Schinkel et al. "Multidrug Resistance and the Role of P-glycoprotein Knockout Mice." *Eur. J. Cancer.* 31A.7-8(1995):1295-1298.

Singh et al. "Raltegravir is a Potent Inhibitor of XMRV, a Virus Implicated in Prostate Cancer and Chronic Fatigue Syndrome." *PLoS ONE.* 4.5(2010):e9948.

Smee et al. "A Review of Compounds Exhibiting Anti-Orthopoxvirus Activity in Animal Models." *Antiviral Res.* 57.1-2(2003):41-52.

Smee et al. "Characterization and Treatment of Cidofovir-Resistant Vaccinia (WR Strain) Virus Infections in Cell Culture and in Mice." *Antiviral Chem. Chemother.* 16.3(2005):203-211.

Smee et al. "Effects of Four Antiviral Substances on Lethal Vaccinia Virus (IHD Strain) Respiratory Infections in Mice." *Int. J. Antimicrob. Agents.* 23.5(2004):430-437.

Tam. "Individual Variation in First -Pass Metabolism." *Clin. Pharmacokinet.* 25.4(1993):300-328.

Toth et al. "Hexadcyloxypropyl-Cidofovir, CMX001, Prevents Adenovirus-Induced Mortality in a Permissive, Immunosuppressed Animal Model." *PNAS.* 105.20(2008):7293-7297.

Wan et al. "Alkoxyalkyl Esters of Cidofovir and Cyclic Cidofovir: Effects of Alkyl Chain Length, Unsaturation, and Substitution on the in vitro Antiviral Activity in Cells Infected with HSV-1 and HCMV." *224th ACS National Meeting.* Boston, MA. Aug. 18-22, 2002. (Abstract #MEDI-30).

Wan et al. "Comparison of the Antiviral Activities of Alkoxyalkyl and Alkyl Esters of Cidofovir Against Human and Murine Cytomegalovirus Replication In Vitro." *Antimicrob. Agents Chemother.* 49.2(2005):656-662.

Wan et al. "Dimethylformamide as a Carbon Monoxide Source in Fast Palladium-Catalyzed Aminocarbonylations of Aryl Bromides." *J. Org. Chem.* 67.17(2002):6232-6235.

Wawzonek et al. "Preparation of Long Chain Alkyl Hydroperoxides." *J. Org. Chem.* 25.4(1960):621-623.

Williams-Aziz et al. "Comparative Activities of Lipid Esters of Cidofovir and Cyclic Cidofovir Against Replication of Herpesviruses In Vitro." *Antimicrob. Agents Chemother.* 49.9(2005):3724-3733.

Yang et al. "An Orally Bioavailable Antipoxvirus Compound (ST-246) Inhibits Extracellular Virus Formation and Protects Mice from Lethal Orthopoxvirus Challenge." *J. Virol.* 79.20(2005):13139-13149.

Lederman. "Progressive Vaccinia in a Military Smallpox Vaccinee—United States 2009." *Center for Disease Control.* May 19, 2009. Web. Retrieved Jan. 3, 2013. http://www.cdc.gov/mmwr/preview/mmwrhtml/mm58e0519a1.html.

COMPOUNDS, COMPOSITIONS AND METHODS FOR TREATING OCULAR CONDITIONS

RELATED APPLICATIONS

This application is a national stage application, filed under 35 U.S.C. §371, of International Application No. PCT/US2010/042749, filed on Jul. 21, 2010, which claims the benefit of and priority to U.S. Provisional Patent Application Ser. No. 61/227,148, filed Jul. 21, 2009, and U.S. Provisional Patent Application Ser. No. 61/332,305, filed May 7, 2010, the disclosures of which are incorporated herein by reference in their entireties.

FIELD OF THE INVENTION

The present invention generally relates to lipid conjugated compounds, derivatives and analogues thereof and methods for treating ocular conditions.

BACKGROUND OF THE INVENTION

Viral infections of the eye (for example, conjunctiva) are one of the most common conditions seen in clinical practice. Viral infection of the eye may be caused by a variety of viruses. However, herpes simplex virus (HSV), varicella zoster virus (VZV) and adenovirus cause the majority of viral infections of conjunctiva. Adenovirus caused conjunctivitis is the leading cause of infectious "pink eye", a highly contagious disease in adults and children which can result in lost days of school and work. In addition, herpes keratitis, caused by HSV, is a serious infection of the cornea. It is the leading cause of infectious blindness in the United States and one of the leading causes of infectious blindness worldwide.

Currently, there is no topic or oral ophthalmic product approved for broad-spectrum antiviral use. In addition, there is also no satisfactory treatment for posterior ocular condition such as macular degeneration. Therefore, there is an industry need to develop an effective ophthalmic composition for treatment of viral infections of the eye and posterior ocular conditions such as macular degeneration.

SUMMARY OF THE INVENTION

One aspect of the present invention provides methods of treating viral infection of the eye. The methods comprise administering a pharmaceutical composition to a subject. The pharmaceutical composition comprises a pharmaceutical acceptable carrier and a compound having the structure of Formula II or III

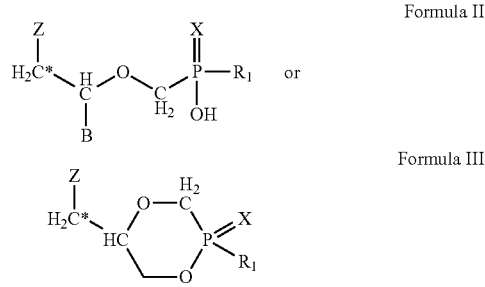

Formula II

Formula III wherein:

X is O, $R_1$ is a moiety selected from the group consisting of optionally substituted alkylglycerol, alkylpropanediol, 1—S-alkylthioglycerol, alkoxyalkanol and alkylethanediol, wherein $R_1$ is linked to —P(=O)— via oxygen of an available —OH of the moiety, B is selected from the group consisting of hydrogen, F, —CF$_3$, —CH$_3$, —CH$_2$CH$_3$, —CH$_2$OH, —CH$_2$CH$_2$OH, —CH(OH)—CH$_3$, —CH$_2$F, —CH=CH$_2$, and —CH$_2$N$_3$, Z is a heterocyclic moiety, and the symbol * indicates the point of attachment of the methylene moiety in Formula (II) or (III) to Z is via an available nitrogen of the heterocyclic moiety, or a pharmaceutically acceptable salt thereof.

In some embodiments, the pharmaceutical acceptable carrier is an ophthalmically acceptable carrier.

In some embodiments, $R_1$ is —O—(CH$_2$)$_a$—O—(CH$_2$)$_t$—CH$_3$, wherein a is 2 to 4 and t is 11 to 19. In other embodiments, a is 3 and t is 15 or 17.

In some embodiments, Z is selected from the group consisting of 6-alkylpurine, $N^6$-alkylpurines, $N^6$-acylpurines, $N^6$-benzylpurine, 6-halopurine, $N^6$-acetylenic purine, $N^6$-acyl purine, $N^6$-hydroxyalkyl purine, 6-thioalkyl purine, $N^2$-alkylpurines, $N^4$-alkylpyrimidines, $N^4$-acylpyrimidines, 4-halopyrimidines, $N^4$-acetylenic pyrimidines, 4-amino and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl.

In one embodiment, Z is purine or pyrimidine.

In one embodiment, Z is

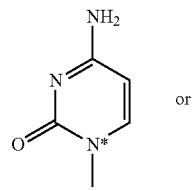

Formula A or

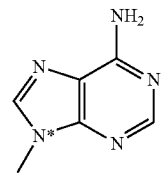

Formula B wherein the symbol * in Formula A or B indicates the point of attachment of N to the methylene in Formula II or III.

In some embodiments, the compound has the structure of:

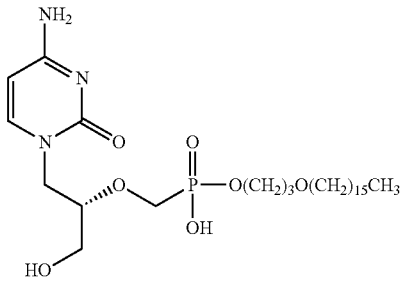

CMX001 (HDP—CDV or HDP—HPMPC)

or a pharmaceutically acceptable salt thereof.

In another embodiment, the compound has the structure of

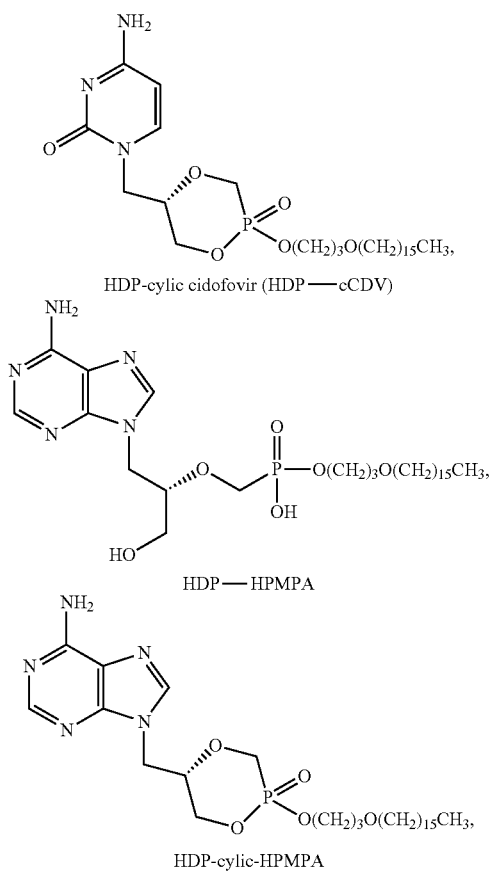

HDP-cylic cidofovir (HDP—cCDV)

HDP—HPMPA

HDP-cylic-HPMPA or a pharmaceutically acceptable salt thereof.

In one embodiment, at least one viral infection is selected from cytomegalovirus, varicella zoster virus, adenovirus, herpes simplex virus or Epstein-Barr virus.

In some embodiments, the pharmaceutical composition is topically administered. In another embodiment, the pharmaceutically composition is orally administered. Further, in some embodiments, the pharmaceutical composition is administered by intraocular injection. In one embodiment, the pharmaceutical composition is administered to the ocular region of the eye.

A further aspect of the invention is ophthalmic compositions comprising compounds described herein and an ophthalmically acceptable carrier.

One aspect of the invention provides a topical ophthalmic composition comprising a topical ophthalmic carrier and the compounds described herein.

Another aspect of the invention provides methods of treating macular degeneration, retinopathy, or retinitis pigmentosa using the pharmaceutical compositions described herein. In some embodiments, the pharmaceutical composition is intraocularly administered. A further aspect of the invention provides a pharmaceutical composition for intraocular administration.

Objects of the present invention will be appreciated by those of ordinary skill in the art from a reading of the detailed description of some embodiments which follow, such description being merely illustrative of the present invention.

DETAILED DESCRIPTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology and virology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. Definitions

As used herein, the term "alkyl" or "alkyl group," refers to a straight-chain (i.e., unbranched) or branched hydrocarbon chain that is completely saturated. In certain embodiments, alkyl groups contain 1-24 carbon atoms. In still other embodiments, alkyl groups contain 11-19 carbon atoms. In some embodiments, the alkyl group contains 15 carbon atoms. In some embodiments, the alkyl group contains 17 carbon atoms. Exemplary alkyl groups include methyl, ethyl, propyl, isopropyl, butyl, isobutyl, pentyl, isopentyl, neopentyl, hexyl, isohexyl, hexadecyl and octadecyl.

As used herein, the term "alkenyl" or "alkenyl group," refers to a straight-chain (i.e., unbranched) or branched hydrocarbon chain that has one or more double bonds. In certain embodiments, alkenyl groups contain 2-24 carbon atoms. In still other embodiments, alkenyl groups contain 11-19 carbon atoms, and in yet other embodiments, alkenyl groups contain 15 carbon atoms. In some embodiments, the alkenyl group contains 17 carbon atoms. Exemplary alkenyl groups include —CH=CH$_2$, —CH$_2$CH=CH$_2$ (also referred to as propenyl), —CH=CHCH$_3$, —CH$_2$CH$_2$CH=CH$_2$, —CH$_2$CH=CHCH$_3$, —CH=CH—CH$_2$CH$_3$, —CH$_2$CH$_2$CH$_2$CH=CH$_2$, —CH=CHCH$_2$CH$_2$CH$_3$, —CH$_2$CH=CHCH$_2$CH$_3$, —CH$_2$CH$_2$CH=CHCH$_3$, —CH$_2$CH$_2$CH$_2$CH=CHCH$_3$, —CH$_2$CH=CH$_2$, —CH=CHCH$_2$CH$_2$CH$_2$CH$_3$, —CH$_2$CH=CHCH$_2$CH$_2$CH$_3$, —CH$_2$CH$_2$CH=CHCH$_2$CH$_3$, —CH$_2$CH$_2$CH$_2$CH=CHCH$_3$, and —CH$_2$CH=CHCH$_2$CH=CH$_2$.

As used herein, the term "alkynyl" or "alkynyl group," refers to a straight-chain (i.e., unbranched) or branched hydrocarbon chain that has one or more triple bonds. In certain embodiments, alkynyl groups contain 2-24 carbon atoms. In still other embodiments, alkynyl groups contain 11-19 carbon atoms, and in yet other embodiments, alkynyl groups contain 15 carbon atoms. In some embodiments, the alkynyl group contains 17 carbon atoms. Exemplary alkynyl groups include —C≡CH, —CH$_2$C≡CH, —C≡CCH$_3$, —CH$_2$CH$_2$C≡CH, —CH$_2$C≡CCH$_3$, —C≡C—CH$_2$CH$_3$, —CH$_2$CH$_2$CH$_2$C≡CH, —C≡CCH$_2$CH$_2$CH$_3$, —CH$_2$C≡CCH$_2$CH$_3$, —CH$_2$CH$_2$C≡CCH$_3$, —CH$_2$CH$_2$CH$_2$CH$_2$C≡CH, —C≡CCH$_2$CH$_2$CH$_2$CH$_3$, —CH$_2$C≡CCH$_2$CH$_2$CH$_3$, —CH$_2$CH$_2$C≡CCH$_2$CH$_3$, and —CH$_2$CH$_2$CH$_2$C≡CCH$_3$.

As used herein, the term "alkoxy", or "thioalkyl", refers to an alkyl group, as previously defined, attached to the principal carbon chain through oxygen ("alkoxy") or sulfur ("thioalkyl") atom.

As used herein, the term "alkylamino" refers to a group having the structure —NR'R" wherein R' and R" are independently alkyl, as defined herein. The term "aminoalkyl" refers to a group having the structure H$_2$NR'—, wherein R' is alkyl, as defined herein. In certain embodiments, the alkyl group contains 1-24 carbon atoms. In certain other embodiments, the alkyl group contains 1-10 carbon atoms. In still other embodiments, the alkyl group contains 1-8 or 1-6 carbon atoms. In yet other embodiments, the alkyl group contains 1-4 carbon atoms. Exemplary alkylamino include, but are not limited to, methylamino, ethylamino, iso-propylamino.

As used herein, the term "aryl" refers to an unsaturated aromatic carbocyclic group of from 6 to 14 carbon atoms having a single ring (e.g., phenyl) or multiple condensed rings (e.g., naphthyl or anthryl). Exemplary aryl, include, but are not limited to, phenyl, naphthyl, tetrahydronaphthyl, indanyl and indenyl.

The term "cycloalkyl", as used herein, refers to cyclic saturated hydrocarbon groups with three to ten carbon atoms having a single ring or multiple condensed ring system. In some embodiments, the cycloalkyl group has three to six carbon atoms. Exemplary cycloalkyl groups include, but are not limited to, cyclopropyl, cyclobutyl, cyclopentyl, cyclohexyl, cycloheptyl and the like. As used herein, the term "cylcoalkenyl" refers to cyclic unsaturated hydrocarbon groups having one or more double bonds with three to ten carbon atoms. In some embodiments, the cycloalkenyl group has three to six carbon atoms.

As used herein, the term "heteroaryl", as used herein, refers to aromatic 5-8 membered monocyclic, 8-12 membered bicyclic, or 11-14 membered tricyclic ring systems containing one or more heteroatoms (such as O, N, S or Se) as part of the ring structure. Examples of heteroaryl groups include, but are not limited to, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, 1,3-selenazole, and benzo[d][1,3]selenazole.

As used herein, the term "halogen" refers to fluorine (F), chlorine (CO, bromine (Br), or iodine (I) and the term "halo" refers to the halogen radicals: fluoro (—F), chloro (—Cl), bromo (—Br), and iodo (—I).

As used herein, the term "haloalkyl" refers to an alkyl group, as defined above, having one, two, or three halogen atoms attached thereto. Examples of haloalkyl groups include, but are not limited to, chloromethyl, bromoethyl, trifluoromethyl, dichloromethyl, etc.

The term "heterocycloalkyl" or "heterocycle", as used herein, refers to a non-aromatic, saturated or unsaturated, 5-, 6- or 7-membered ring or a polycyclic group, including, but not limited to a bi- or tri-cyclic having between one or more heteroatoms independently selected from oxygen, sulfur and nitrogen as part of the ring, wherein (i) each 5-membered ring has 0 to 1 double bonds and each 6-membered ring has 0 to 2 double bonds, (ii) the nitrogen and sulfur heteroatoms may be optionally oxidized, (iii) the nitrogen heteroatom may optionally be quaternized, and/or (iv) any of the above heterocyclic rings may be fused to a benzene ring. Exemplary heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

In some embodiments, alkyl, alkenyl, alkynyl, alkoxy, cycloalkyl, cycloalkenyl, heterocycloalkyl, aryl, heteroaryl, described herein include both substituted and unsubstituted moieties. Exemplary substituents include, but are not limited to, halo, hydroxyl, amino, amide, —SH, cyano, nitro, thioalkyl, carboxylic acid, —NH—C(=NH)—NH$_2$, alkyl, alkenyl, alkynyl, aryl, heteroaryl, cycloalkyl, heterocycloalkyl, in which alkyl, alkenyl, alkynyl, alkoxyl, aryl, heteroaryl, cycloalkyl, and heterocycloalkyl may be further substituted.

As used herein, the term "amino acid" refers to a compound comprising a primary amino (—NH$_2$) group and a carboxylic acid (—COOH) group. The amino acids used in the present invention include naturally occurring and synthetic α, β, γ or δ amino acids (or D or L amino acid), and includes but are not limited to, amino acids found in proteins. Exemplary amino acids include, but are not limited to, glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid may be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. Additionally, as used herein, "amino acids" also include derivatives of amino acids such as esters, and amides, and salts, as well as other derivatives, including derivatives having pharmacoproperties upon metabolism to an active form.

As used herein, the term "natural a amino acid" refers to a naturally occurring α-amino acid comprising a carbon atom bonded to a primary amino (—NH$_2$) group, a carboxylic acid (—COOH) group, a side chain, and a hydrogen atom. Exemplary natural a amino acids include, but are not limited to, glycine, alanine, valine, leucine, isoleucine, methionine, phenylalanine, tryptophane, proline, serine, threonine, cysteine, tyrosine, asparaginate, glutaminate, aspartate, glutamate, lysine, arginine and histidine.

As used herein, "subject", as used herein, means a mammalian subject (e.g., dog, cat, horse, cow, sheep, goat, monkey, etc.), and particularly human subjects (including both male and female subjects, and including neonatal, infant, juvenile, adolescent, adult and geriatric subjects, and further including various races and ethnicities including, but not limited to, white, black, Asian, American Indian and Hispanic.

As used herein, "treatment", "treat", and "treating" refer to reversing, alleviating, or inhibiting the progress of a disorder or disease as described herein.

As used herein, "prevention", "prevent", and "preventing" refer to eliminating or reducing the incidence or onset of a disorder or disease as described herein, as compared to that which would occur in the absence of the measure taken.

As used herein "an effective amount" refers to an amount that causes relief of symptoms of a disorder or disease as noted through clinical testing and evaluation, patient observation, and/or the like. An "effective amount" can further designate a dose that causes a detectable change in biological or chemical activity. The detectable changes may be detected and/or further quantified by one skilled in the art for the relevant mechanism or process. Moreover, an "effective amount" can designate an amount that maintains a desired physiological state, i.e., reduces or prevents significant decline and/or promotes improvement in the condition of interest. In some embodiments, an "effective amount" can further refer to a therapeutically effective amount.

Furthermore, it will be appreciated by one of ordinary skill in the art that the synthetic methods, as described herein, utilize a variety of protecting groups. As used herein, the term "protecting group" refers to a particular functional moiety, e.g. O, S, or N, that is temporarily blocked so that a reaction can be carried out selectively at another reactive site in a multifunctional compound. Protecting groups may be introduced and removed at appropriate stages during the synthesis of a compound using methods that are known to one of ordinary skill in the art. The protecting groups are applied according to standard methods of organic synthesis as described in the literature (Theodora W. Green and Peter G. M. Wuts (2007) *Protecting Groups in Organic Synthesis*, 4$^{th}$ edition, John Wiley and Sons, incorporated by reference with respect to protecting groups).

Exemplary protecting groups include, but are not limited to, oxygen, sulfur, nitrogen and carbon protecting groups. For example, oxygen protecting groups include, but are not limited to, methyl ethers, substituted methyl ethers (e.g., MOM (methoxymethyl ether), MTM (methylthiomethyl ether), BOM (benzyloxymethyl ether), PMBM (p-methoxybenzyloxymethyl ether), optionally substituted ethyl ethers, optionally substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), esters (e.g. formate, acetate, benzoate (Bz), trifluoroacetate, dichloroacetate) carbonates, cyclic acetals and ketals. In addition, exemplary nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives, etc. Certain other exemplary protecting groups are detailed herein, however, it will be appreciated that the present invention is not intended to be limited to these protecting groups; rather, a variety of additional equivalent protecting groups may be utilized according to methods known to one skilled in the art.

Unless indicated otherwise, it should be understood that a chemical group described herein by its chemical formula, including a bond moiety by a "—", is attached to the rest of the molecule at the indicated "—". For example, the group —SO$_2$phenyl is attached to the rest of the molecule at the left-hand side via the indicated bond.

As used herein, the eye includes the eyeball and the tissues and fluids which constitute the eyeball, the periocular muscles (such as the oblique and rectus muscles) and the portion of the optic nerve which is within or adjacent to the eyeball. For example, the eye includes, but is not limited to, eye ball, cornea, conjunctiva, retina, lens, vitreous humour and iris.

B. Compounds

According to some aspects of the present invention, compounds with a range of biological properties are provided. Compounds described herein have biological activities relevant for the treatment of viral infection of the eye. In some embodiments, compounds described herein have biological activities relevant for the treatment of posterior ocular conditions (e.g. macular degeneration, retinopathy, or retinitis pigmentosa).

In some embodiments, the compounds of the present invention have the structure of Formula I:

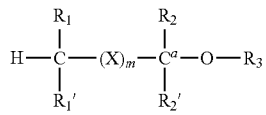

wherein:

R$_1$, R$_1$', R$_2$ and R$_2$' are independently —H, optionally substituted —O(C$_1$-C$_{24}$)alkyl, —O(C$_2$-C$_{24}$)alkenyl, —O(C$_2$-C$_{24}$)alkynyl, —O(C$_1$-C$_{24}$)acyl, —S(C$_1$-C$_{24}$)alkyl, —S(C$_2$-C$_{24}$)alkenyl, —S(C$_2$-C$_{24}$)alkynyl, or —S(C$_1$-C$_{24}$)acyl, —N(C$_1$-C$_{24}$)acyl, —NH(C$_2$-C$_{24}$)alkyl, —NH(C$_2$-C$_{24}$)alkeyl, —NH(C$_2$-C$_{24}$)alkynyl, —N((C$_1$-C$_{24}$)alkyl)$_2$, oxo, halogen, —NH$_2$, —OH, or —SH;

wherein at least one of R$_1$ and R$_1$' are not —H, and said alkyl, alkenyl, alkynyl or acyl moieties optionally have 1 to 6 double bonds or triple bonds, R$_3$ is a pharmaceutically active phosphonate, bisphosphonate or a phosphonate derivative of a pharmacologically active compound;

X, when present, is:

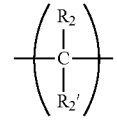

and in is an integer from 0 to 6.

In some embodiments, m is 0, 1 or 2. In one embodiment, R$_2$ and R$_2$' are H. In another embodiment, the compounds are ethanediol, propanediol or butanediol derivatives of a therapeutic phosphonate. In one embodiment, the compounds of the present invention are ethanediol phosphonate species that have the structure:

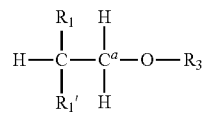

wherein R$_1$, R$_1$', and R$_3$ are as defined above.

In some embodiments, the compounds of the present invention are propanediol species that have the structure:

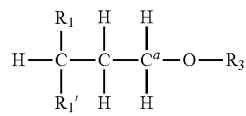

wherein m is 1 and R$_1$, R$_1$', and R$_3$ are as defined above in the general formula.

In one embodiment, the compounds of the present invention are glycerol species that have the structure:

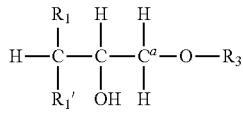

wherein in is 1, $R_2$ is H, $R_2'$ is OH, and $R_2$ and $R_2'$ on $C^\alpha$ are both —H. Glycerol is an optically active molecule. Using the stereospecific numbering convention for glycerol, the sn-3 position is the position which is phosphorylated by glycerol kinase. In compounds of the invention having a glycerol residue, the $R_3$ moiety may be joined at either the sn-3 or sn-1 position of glycerol.

In some embodiments, $R_1$ is an alkoxy group having the formula —O—$(CH_2)_t$—$CH_3$, wherein t is 0-24, In one embodiment, t is 11-19. In another embodiment, t is 15 or 17.

Additionally, antiviral phosphonates such as cidofovir, cyclic-cidofovir, adefovir, tenofovir, and the like, may be used as an $R_3$ group in accordance with the present invention.

According to one aspect of the present invention, the antiviral compounds having the structure of Formula II or III

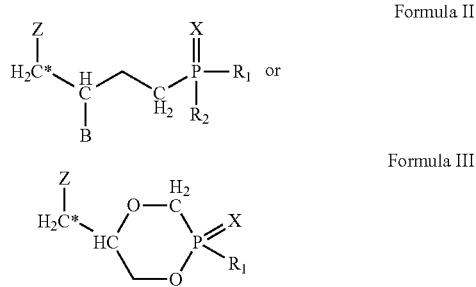

wherein:
$R_1$ is a moiety selected from the group consisting of alkylglycerol, alkylpropanediol, 1—S-alkylthioglycerol, alkoxyalkanol and alkylethanediol, wherein $R_1$ is linked to —P(=X)— via oxygen of an available —OH of the moiety,
B is selected from the group consisting of hydrogen, —$CH_3$, —$CH_2CH_3$, —$CH_2OH$, —$CH_2CH_2OH$, —CH(OH)$CH_3$, —$CH_2F$, —CH=$CH_2$, and —$CH_2N_3$,
X is selenium, sulphur, or oxygen (in some embodiments, oxygen);
$R_2$ is hydroxy, —$OR_{2a}$, —$BH_3$, $C_{1-8}$ alkyl, $C_{2-8}$ alkenyl, $C_{2-8}$ alkynyl, $C_{1-8}$ heteroalkyl, $C_{2-8}$ heteroalkenyl, $C_{2-8}$ heteroalkynyl, or —NR'H (in some embodiments, $R_2$ is hydroxyl);
$R_{2a}$ is $C_{1-8}$ alkyl, $C_{2-8}$ alkenyl, $C_{2-8}$ alkynyl, $C_{1-8}$ heteroalkyl, $C_{2-8}$ heteroalkenyl, $C_{2-8}$ heteroalkynyl, —P(=O)(OH)$_2$, or —P(=O)(OH)OP(=O)(OH)$_2$,
R' is $C_{1-3}$ alkyl, $C_{2-8}$ alkenyl, $C_{2-8}$ alkynyl, $C_{1-8}$ heteroalkyl, $C_{2-8}$ heteroalkynyl, $C_{2-8}$ heteroalkenyl, $C_{6-10}$ aryl, or an substituted or unsubstituted amino acid residue,
Z is a heterocyclic moiety, and
the symbol * indicates the point of attachment of the methylene moiety in Formula (II) or (III) to Z is via an available nitrogen of the heterocyclic moiety,
or a pharmaceutically acceptable salt thereof.
In some embodiments, the antiviral compound is in the form of an enantiomer, diastereomer, racemate, stereoisomer, tautomer, rotamer or a mixture thereof.

In one embodiment, $R_1$ is a moiety of

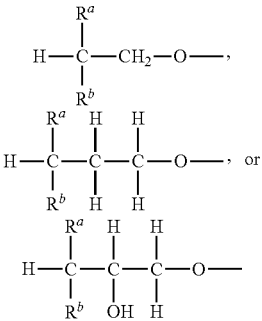

wherein $R^a$ and $R^b$ are independent selected from the group consisting of —H, optionally substituted —O($C_1$-$C_{24}$)alkyl, O($C_2$ $C_{24}$)alkenyl, O($C_2$-$C_{24}$)alkynyl, —O($C_1$-$C_{24}$)acyl, —S($C_1$-$C_{24}$)alkyl, S($C_2$-$C_{24}$)alkenyl, —S($C_2$-$C_{24}$)alkynyl, or —S($C_1$-$C_{24}$)acyl, —NH($C_1$-$C_{24}$)acyl, —NH($C_1$-$C_{24}$) alkyl, NH($C_2$-$C_{24}$)alkeyl, —NH($C_2$-$C_{24}$)alkynyl, —N(($C_1$-$C_{24}$)alkyl)$_2$, oxo, halogen, —$NH_2$, —OH and SH. In some embodiments, at least one of $R^a$ or $R^b$ is not hydrogen. In some embodiments, $R^a$ and $R^b$ are independent selected from the group consisting of —H, optionally substituted —O($C_1$-$C_{24}$)alkyl, —O($C_2$-$C_{24}$)alkenyl, —O($C_2$-$C_{24}$)alkynyl, O($C_1$-$C_{24}$)acyl, —S($C_1$-$C_{24}$)alkyl, —S($C_2$-$C_{24}$)alkenyl, —S($C_2$-$C_{24}$)alknyl or —S($C_1$-$C_{24}$)acyl.

In another embodiment, $R_1$ is a moiety of alkylethanediol or alkylpropanediol. Yet, in one embodiment, $R_1$ is a moiety of hexadecylpropanediol. Further, in some embodiments, $R_1$ is a moiety of octadecylpropanediol. In another embodiment, $R_1$ is —O—$(CH_2)_a$—O—$(CH_2)_t$—$CH_3$, wherein a is 2 to 4 and t is 11 to 19. In some embodiments, a is 3 and t is 15 or 17.

In some embodiments, Z is purine or pyrimidine, which may be optionally substituted by at least one substituent. In some embodiments, at least one substituent may be selected from the group consisting of halogen, hydroxyl, amino, substituted amino, di-substituted amino, sulfur, nitro, cyano, acetyl, acyl, aza, $C_{1-6}$ alkyl, $C_{2-6}$ alkenyl, $C_{2-6}$ alkynyl, $C_{6-10}$ aryl, and carbonyl substituted with a $C_{1-6}$ alkyl, $C_{2-6}$ alkenyl, $C_{2-6}$ alkynyl, or $C_{6-10}$ aryl, haloalkyl and aminoalkyl.

In some embodiments, Z is selected from adenine, 6-chloropurine, xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, thymine, cytosine, 5-fluorocytosine, uracil; 5-bromouracil, 5-iodouracil, 5-ethyluracil, 5-ethynyluracil, 5-propynyluracil, 5-propyluracil, 5-vinyluracil, or 5-bromovinyluracil. In some embodiments, Z is selected from guanin-9-yl, adenin-9-yl, 2,6-diaminopurin-9-yl, 2-aminopurin-9-yl or their 1-deaza, 3-deaza, 8-aza compounds, or cytosin-1-yl.

In another embodiment, exemplary Z includes, but is not limited to, 6-alkylpurine and $N^6$-alkylpurines, $N^6$-acylpurines, $N^6$-benzylpurine, 6-halopurine, $N^6$-acetylenic purine, $N^6$-acyl purine, $N^6$-hydroxyalkyl purine, 6-thioalkyl purine, $N^2$-alkylpurines, $N^4$-alkylpyrimidines, $N^4$-acylpyrimidines, 4-halopyrimidines, $N^4$-acetylenic pyrimidines, 4-amino and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl. Preferred bases include cytosine, 5-fluorocytosine, uracil, thymine, adenine, guanine, xanthine, 2,6-diaminopurine, 6-aminopurine, 6-chloropurine and 2,6-dichloropurine.

In one embodiment, Z is

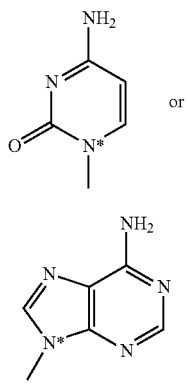

wherein the symbol * in Formula A or B indicates the point of attachment of N to the methylene in Formula II or III.

Additional examples of Z include, but are not limited to, moieties of the general formula:

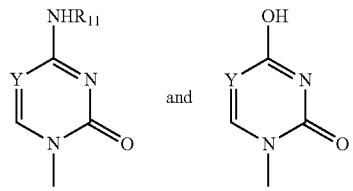

where:
Y is N or CX;
X is selected from the group consisting of H, halo, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl, and $COR_b$;
$R_b$ is selected from the group consisting of H, OH, SH, $C_{1-6}$ alkyl, $C_{1-6}$ aminoalkyl, $C_{1-6}$ alkoxy and $C_{1-6}$ thioalkyl; and
$R_{11}$ is selected from the group consisting of H, $C_{1-6}$ alkyl, $C_{2-6}$ alkenyl, $C_{2-6}$ alkynyl, $C_{3-6}$ cycloalkyl, $C_{4-12}$ alkylcycloalkyl, $C_{6-10}$ aryl, and carbonyl substituted with a $C_{1-6}$ alkyl, $C_{2-6}$ alkenyl, $C_{2-6}$ alkynyl, or $C_{6-10}$ aryl. The example of Z is further described in U.S. Pat. No. 6,583,149, which is incorporated by reference in its entirety.

Additional examples of Z include, but are not limited to, compounds of the general formula:

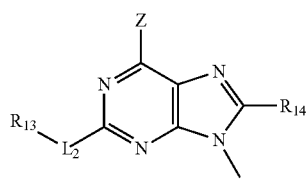

where:
Z is $-NR_aR_b$, or $-OR_2$,
$L_2$ is a covalent bond (that is, is absent), $-N(-R_{15})-$, $N(-R_{15})C(=O)-$, $-O-$, $-S-$, $-S(=O)-$, or is $-S(=O)_2-$, $R_{13}$ is H, $C_{1-6}$ alkyl, $C_{1-6}$ heteroalkyl, $C_{2-6}$ alkenyl, $C_{6-10}$ aryl, $C_{7-16}$ arylalkyl, $C_{3-15}$ carbocyclyl, $C_{6-10}$ heterocyclyl, or $C_{7-16}$ heterocyclylalkyl;

$R_{14}$ is H, halo, hydroxy, alkoxy, $-O(CH_2)_xOC(=O)OR_{15}$, or $OC(=O)OR_{15}$, wherein X is 2 or 3 to 10, 15 or 20, $R_{15}$ is H, $C_{1-6}$ alkyl, $C_{1-6}$ heteroalkyl, $C_{2-6}$ alkenyl, $C_{6-10}$ aryl, $C_{7-16}$ arylalkyl, $C_{3-10}$ cycloalkyl, $C_{6-10}$ heterocyclyl, or $C_{7-16}$ heterocyclylalkyl, and $R_a$, $R_b$ are independently selected from the group consisting of hydrogen, $C_{1-6}$ alkyl, or $C_{3-6}$ cycloalkyl, and $C_{3-8}$ heterocyclyl, wherein $C_{3-6}$ cycloalkyl and $C_{3-8}$ heterocyclyl can be optionally substituted with one or more $C_{1-5}$ alkyl.

Additional examples of Z include, but are not limited to, the moiety of the general formula:

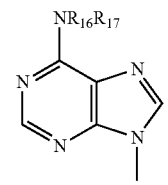

$R_{16}$ and $R_{17}$ are independently selected from the group consisting of hydrogen, $C_{1-6}$ alkyl, or $C_{3-6}$ cycloalkyl, or $C_{3-8}$ heterocyclyl, wherein $C_{3-6}$ cycloalkyl and $C_{3-8}$ heterocyclyl can be optionally substituted with one or more $C_{1-5}$ alkyl.

The exemplary compounds of the present invention include, but are not limited to,

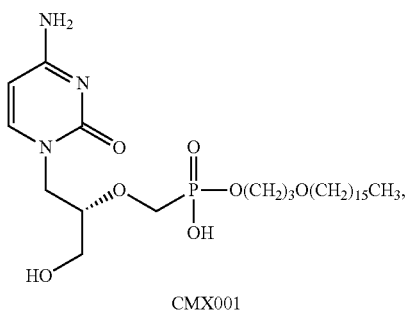

CMX001

HDP-cCDV

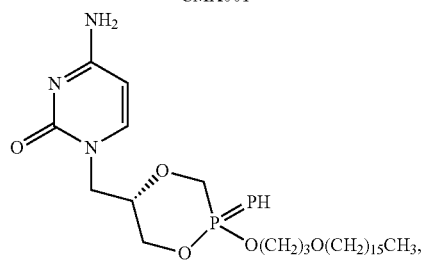

HDP-HPMPA

-continued

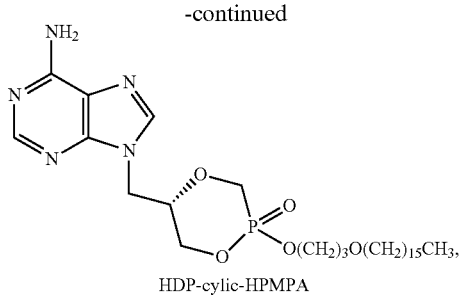

HDP-cylic-HPMPA or a pharmaceutically acceptable salt thereof.

More exemplary compounds are shown below:

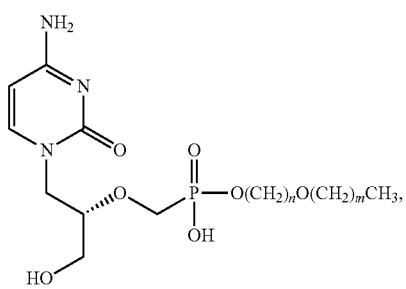

n = 2, m = 17 ODE-CDV
n = 3, m = 17 ODP-CDV

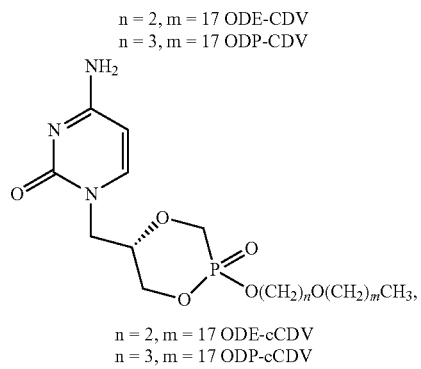

n = 2, m = 17 ODE-cCDV
n = 3, m = 17 ODP-cCDV

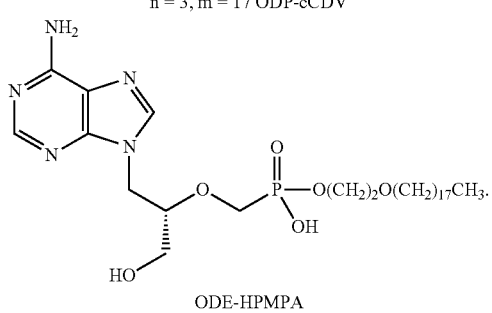

ODE-HPMPA

According to a further aspect of the present invention, a variety of lipid derivatives of acyclic nucleotide phosphonates such as cidofovir, tenofovir, cyclic-cidofovir and adefovir can also be used as active agents in the methods and compositions provided herein. In one embodiment, the active agents have the following structures:

$$H_2C-(W^1)_n-R^1$$
$$HC-(W^2)_m-R^2,$$
$$CH_2-D$$
V $$H_2C-(W^1)_n-R^1,$$
$$CH_2-D$$
VI $$H_2C-(W^1)_n-R^1$$
$$CH_2$$
$$CH_2-D$$
VII $$H_2C-(W^1)_n-R^1,$$
$$(CH_2)_2$$
$$CH_2-D$$
VIII $$CH_2-(W^1)_n-R^1, \text{ or}$$
$$HC-(W^2)_m-R^2$$
$$CH_2$$
$$CH_2-D$$
IX $$CH_2-(W^1)_n-R^1$$
$$HC-(W^2)_m-R^2$$
$$HC-(W^3)_p-R^3$$
$$CH_2-D$$
X wherein $W^1$, $W^2$, and $W^3$ are each independently —O—, —S—, —SO—, —SO$_2$, —O(C=O)—, —(C=O)O—, —NH(C=O)—, —(C=O)NH— or —NH—; and in one embodiment are each independently O, S, or —O(C=O)—;

n is 0 or 1; m is 0 or 1; p is 0 or 1;

$R^1$ is an optionally substituted alkyl, alkenyl or alkynyl, e.g., $C_{4-30}$ alkyl, $C_{2-30}$ alkenyl, or $C_{2-30}$ alkynyl; or in one embodiment, $R^1$ is optionally substituted $C_{8-30}$ alkyl, $C_{8-30}$ alkenyl or $C_{8-30}$ alkynyl, or $R^1$ is a $C_{8-24}$ alkyl, $C_{8-24}$ alkenyl or $C_{8-24}$ alkynyl (e.g., $C_{17}$, $C_{18}$, $C_{19}$, $C_{20}$, $C_{21}$, $C_{22}$, $C_{23}$, or $C_{24}$ alkyl, alkenyl, or alkynyl);

$R^2$ and $R^3$ are each independently an optionally substituted $C_{1-25}$ alkyl, $C_{2-25}$ alkenyl, or $C_{2-25}$ alkynyl;

D may be cidofovir, tenofovir, cyclic cidofovir or adefovir directly linked to a methylene group as depicted in Formulas V-X. For example, when D is tenofovir, D is a moiety of the formula:

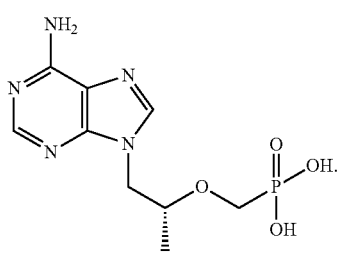 [SMILES: C[C@H](Cn1cnc2c(N)ncnc21)OCP(=O)(O)O]

When D is cidofovir, D is a moiety of the formula:

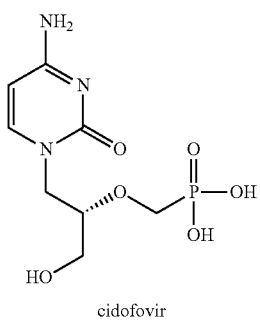 [SMILES: Nc1ccn(C[C@@H](CO)OCP(=O)(O)O)c(=O)n1]

cidofovir (e.g., Cidofovir or tenofovir is directly linked to the methylene group of formula V-X via the phosphonate hydroxyl group).

In some embodiments of formulas V-X:
$W^1$, $W^2$, and $W^3$ are each independently —O—, —S—, or —O(CO)—;
n is 0 or 1; m is 0 or 1; p is 0 or 1;
$R^1$ is optionally substituted $C_{12-24}$ alkyl or alkenyl (e.g., $C_{12}$, $C_{13}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl or alkenyl);
$R^2$ and $R^3$ are each independently optionally substituted $C_{1-24}$ alkyl or $C_{2-24}$ alkenyl, or $C_{2-24}$ alkynyl.
D is cidofovir, tenofovir, cyclic cidofovir or adefovir linked directly to a methylene group as depicted in Formulas V-X.

In another embodiment, the active compound has one of the following structures: wherein $R^1$ is an optionally substituted $C_{8-24}$ alkyl, for example, $C_{12-24}$ alkyl, D is cidofovir, tenofovir, cyclic cidofovir or adefovir linked directly to a methylene group as depicted in Formulas V-X.

Compounds, compositions, formulations, and methods of treating subjects that can be used to carry out the present invention include, but are not limited to, those described in U.S. Pat. Nos. 6,716,825, 7,034,014, 7,094,772, 7,098,197, 7,452,898, and 7,687,480, the disclosures of which are incorporated by reference herein in their entireties.

Certain compounds of the invention possess one or more chiral centers, e.g. in the sugar moieties, and may thus exist in optically active forms. Likewise, when the compounds contain an alkenyl group or an unsaturated alkyl or acyl moiety there is the possibility of cis- and trans-isomeric forms of the compounds. Additional asymmetric carbon atoms can be present in a substituent group such as an alkyl group. The R- and S-isomers and mixtures thereof, including racemic mixtures as well as mixtures of cis- and trans-isomers are contemplated by this invention. All such isomers as well as mixtures thereof are intended to be included in the invention. If a particular stereoisomer is desired, it can be prepared by methods well known in the art by using stereospecific reactions with starting materials that contain the asymmetric centers and are already resolved or, alternatively, by methods that lead to mixtures of the stereoisomer and resolution by known methods.

B. Synthesis of Compounds

The process to be utilized in the preparation of the compounds described herein depends upon the specific compound desired. Such factors as the selection of the specific substituent and various possible locations of the specific substituent all play a role in the path to be followed in the preparation of the specific compounds of this invention. Those factors are readily recognized by one of ordinary skill in the art.

In general, the compounds of this invention may be prepared by standard techniques known in the art and by known processes analogous thereto. General methods for preparing compounds of the present invention are set forth below.

In the following description, all variables are, unless otherwise noted, as defined in the formulas described herein. The following non-limiting descriptions illustrate the general methodologies that may be used to obtain the compounds described herein.

Compounds described in the invention may be prepared in a variety of ways, as generally depicted in Schemes V and VI of U.S. Pat. No., 6,716,825. The general phosphonate esterification methods described below are provided for illustrative purposes only and are not to be construed as limiting this invention in any manner. Indeed, several methods have been developed for direct condensation of phosphonic acids with alcohols (see, for example, R. C. Larock, Comprehensive Organic Transformations, VCH, New York, 1989, p. 966 and references cited therein). Isolation and purification of the compounds and intermediates described in the examples can be effected, if desired, by any suitable separation or purification procedure such as, for example, filtration, extraction, crystallization, flash column chromatography, thin-layer chromatography, distillation or a combination of these procedures. Specific illustrations of suitable separation and isolation procedures are in the examples below. Other equivalent separation and isolation procedures can of course, also be used.

Scheme V of U.S. Pat. No. 6,716,825 illustrates a general synthesis of alkylglycerol or alkylpropanediol analogs of cidofovir, cyclic cidofovir, and other phosphonates. Treatment of 2,3-isopropylidene glycerol, 1, with NaH in dimethylformamide followed by reaction with an alkyl methanesulfonate yields the alkyl ether, 2. Removal of the isopropylidene group by treatment with acetic acid followed by reaction with trityl chloride in pyridine yields the intermediate 3. Alkylation of intermediate 3 with an alkyl halide results in compound 4. Removal of the trityl group with 80% aqueous acetic acid affords the O,O-dialkyl glycerol, 5. Bromination of compound 5 followed by reaction with the sodium salt of cyclic cidofovir or other phosphonate-containing nucleotide yields the desired phosphonate adduct, 7. Ring-opening of the cyclic adduct is accomplished by reaction with aqueous sodium hydroxide. The compound of propanediol species may be synthesized by substituting 1-O-alkylpropane-3-ol for compound 5 in Scheme V. The tenofovir and adefovir analogs may be synthesized by substituting these nucleotide phosphonates for cCDV in reaction (f) of Scheme V. Similarly, other nucleotide phosphonates of the invention may be formed in this manner.

Scheme VI of U.S. Pat. No. 6,716,825 illustrates a general method for the synthesis of nucleotide phosphonates of the invention using 1-O-hexadecyloxypropyl-adefovir as the example. The nucleotide phosphonate (5 mmol) is suspended in dry pyridine and an alkoxyalkanol or alkylglycerol derivative (6 mmol) and 1,3-dicyclohexylcarbodiimde (DCC, 10 mmol) are added. The mixture is heated to reflux and stirred vigorously until the condensation reaction is complete as monitored by thin-layer chromatography. The mixture is then cooled and filtered. The filtrate is concentrated under reduced pressure and the residues adsorbed on silica gel and purified by flash column chromatography (elution with approx. 9:1 dichloromethane/methanol) to yield the corresponding phosphonate monoester.

FIG. 1 of Kern et al., AAC 46 (4):991 illustrates the synthesis for alkoxyalkyl analogs of cidofovir (CDV) and cyclic cidofovir (cCDV). In FIG. 1, the arrows indicate the following reagents: (a) N,N-dicyclohexylmorpholinocarboxamide, N,N-dicyclohexylcarbodiimide, pyridine, 100° C.; (b)

1-bromo-3-octadecyloxyethane (ODE), or 1-bromo-3-hexadecyloxypropane (HDP), N,N-dimethylformamide, 80° C.; (c) 0.5 M NaOH.

One skilled in the art should be able to convert the salt disclosed in the application to free acid by using any applicable methods known to one skilled in the art.

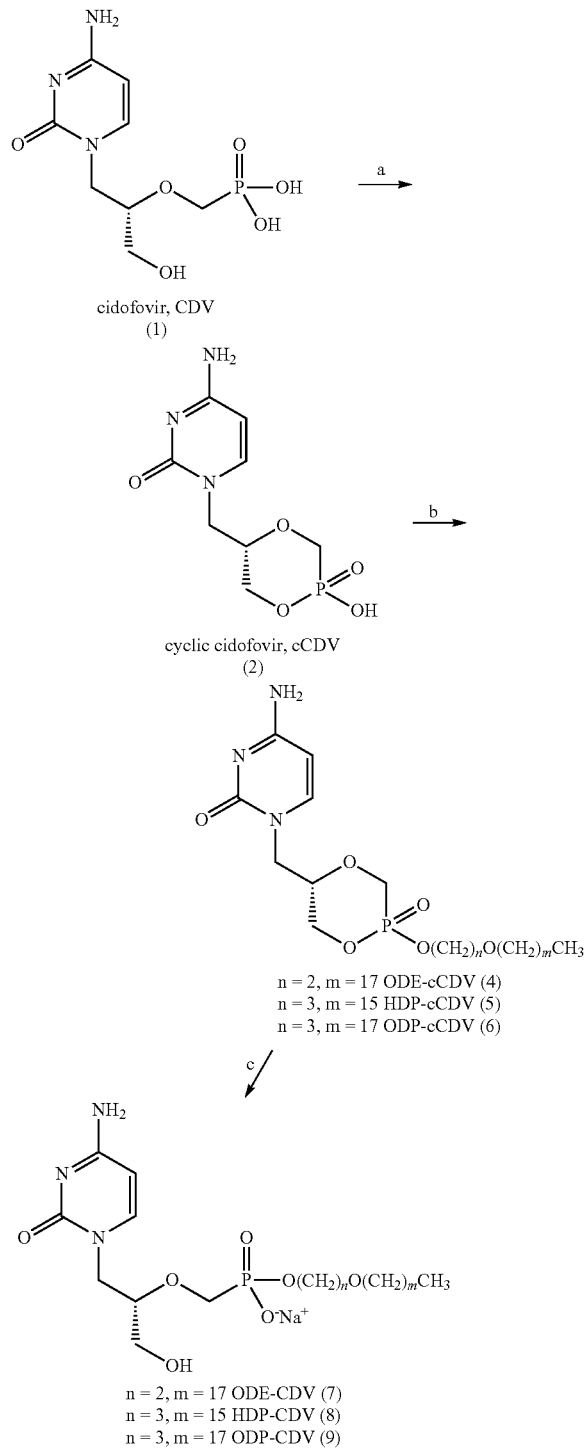

FIG. 1.

As described herein, compounds of the invention may optionally be substituted with one or more substituents, such as are illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention may be those that result in the formation of stable or chemically feasible compounds.

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium; alkaline earth metals such as calcium and magnesium; or derive from ammonium, ammonium salts with organic bases such as dicyclohexylamine and N-methyl-D-glucamine, among numerous other acids well known in the pharmaceutical art. In some embodiments, the pharmaceutically acceptable salts are selected from organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Exemplary agent that may be used to form the salt include, but are not limited to, citric acid, fumaric acid, gentisic acid, hippuric acid, maleic acid, L-mandelic acid, orotic acid, oxalic acid, saccharin, succinic acid, L-tartaric acid, toluenesulfonic acid, ammonia, Larginine, calcium hydroxide, diethylamine, diethylaminoethanol, ethylenediamine, imidazole, L-lysine, 2-hydroxyethylmorpholine, N-methyl-glucamine, potassium methanolate, zinc tert-butoxide.

C. Pharmaceutical Compositions and Administration

According to one aspect of the present invention, a pharmaceutical composition is provided. In some embodiments, the pharmaceutical composition comprises a pharmaceutically acceptable carrier and a compound described herein in an amount effective to treat an ocular condition. In some embodiments, the ocular condition is a viral infection of the eye. In another embodiment, the ocular condition is a posterior ocular condition or a degeneration condition of the retina or retinal nerve, e.g. macular degeneration, retinopathy, retinitis pigmentosa, and a combination thereof.

Further, in one embodiment, the pharmaceutically acceptable composition is an ophthalmically acceptable composition and the pharmaceutically acceptable carrier is an ophthalmically acceptable carrier.

As used herein, the term "ophthalmically acceptable" is defined as to a formulation, composition or ingredient herein having no persistent harmful effect on the treated eye or the functioning thereof, or on the general health of the subject being treated. It will be recognized that transient effects such as minor irritation or a "stinging" sensation are common with topical ophthalmic administration of drugs and the existence of such transient effects is not inconsistent with the formulation, composition or ingredient in question being "ophthalmically acceptable" as herein defined.

The compositions of the invention may be administered in topical formulations or polymer matrices, hydrogel matrices, polymer implants, or encapsulated formulations to allow slow or sustained release of the compositions. In some embodiments, the composition described herein is an aqueous solution, suspension or solution/suspension, which can be presented in the form of eye drops. A composition of the invention may be in the form of a liquid wherein the active agent is present in solution, in suspension or both. The term "solution/suspension" herein refers to a liquid composition wherein a first portion of the active agent is present in solution and a second portion of the active agent is present in particulate form, in suspension in a liquid matrix. A liquid composition herein includes a gel. In some embodiments, the liquid composition is aqueous. In other embodiment, the composition can take the form of an ointment or cream.

In some embodiments, the ophthalmic composition further comprises a penetration enhancer. In one embodiment, the penetration enhancer is present in an amount in the range of about 0.001 wt. % to about 5 wt. %.

In another embodiment, the ophthalmically acceptable carrier comprises an aqueous solution, a non aqueous solution, or an emulsion, etc. (for example, water, oil, wax, grease or petrolatum or a combination thereof). Exemplary aqueous carriers include, but are not limited to water, buffered water, 0.8% saline, 0.3% glycine, hyaluronic acid, phospholipid carriers or artificial tears carriers, or mixtures of such carriers and the like. As used in this paragraph, the term "phospholipid" refers to the phospholipids of the phospholipid carrier. Exemplary phospholipid carriers and artificial tears carriers include but are not limited to those described in U.S. Pat. No. 6,645,978, which is incorporated herein.

An aqueous suspension or solution/suspension of the invention can contain one or more polymers as suspending agents. Exemplary polymers include, but are not limited to, water-soluble polymers such as cellulosic polymers, e.g., hydroxypropyl methylcellulose, and water-insoluble polymers such as cross-linked carboxyl-containing polymers. In some embodiments, the polymer may include hydroxypropyl methylcellulose, guar gum, carboxyvinyl polymers (acrylic acid polymer), hydroxyethyl cellulose, carboxymethylcellulose, poly(methylmethacrylate), polyacrylamide, polycarbophil, polyethylene oxide, acrylic acid/butyl acrylate copolymer, sodium alginate and dextran.

Any excipients known to one skilled in the art may be included in the compositions of the present invention to increase retention of the composition in an eye. Exemplary excipients include, but are not limited to, monomeric polyols, such as, glycerol, propylene glycol, ethylene glycol; polymeric polyols, such as, polyethylene glycol, hydroxypropylmethyl cellulose ("HPMC"), carboxy methylcellulose sodium, hydroxy propylcellulose ("HPC"), dextrans, such as, dextran 70; water soluble proteins, such as gelatin; and vinyl polymers, such as, polyvinyl alcohol, polyvinyl/pyrrolidone povidone and carbomers, such as, carbomer 934P, carbomer 941, carbomer 940, carbomer 974; phydroxyethylcellulose; methylcellulose; polyvinylpyrrolidone; polysaccharides, such as hyaluronic acid and its salts; chondroitin sulfate and its salts; dextrans; various polymers of the cellulose family; vinyl polymers; and acrylic acid polymers.

In some embodiments, the ophthalmic composition further comprises at least one viscosifier. In one embodiment, at least one viscosifier is selected from natural polysaccharides, natural gums, modified natural polymers, synthetic polymers, proteins and synthetic polypeptides that are capable of increasing viscosity and are ophthalmically acceptable. In some embodiments, at least one viscosifier is a mucomimetic. In one embodiment, at least one viscosifier is a carboxyvinyl polymer.

In another embodiment, the ophthalmically acceptable carrier is a topically acceptable carrier. Exemplary topically acceptable carriers include, but are not limited to, solution such as water, suspension, oil, wax, grease, petrolatum, or a combination thereof.

In some embodiments, the ophthalmic composition described herein comprises at least excipients selected from buffers, surfactants, stabilizers, preservatives, ophthalmic wetting agents, or ophthalmic diluting agents.

Wetting agents commonly used in ophthalmic solutions include carboxymethylcellulose, hydroxypropyl methylcellulose, glycerin, mannitol, polyvinyl alcohol or hydroxyethylcellulose. The diluting agent may be water, distilled water, saline solution, sterile water, artificial tears, etc. wherein the wetting agent is present in an amount of about 0.001% to about 30%.

In another embodiment, the ophthalmic pharmaceutical composition further comprises one or more additional active ophthalmic pharmaceutical agent such as anti inflammatory agents, antibiotics, anti fungals, anti virus, ocular hypotensive agents, local anesthetic agents, cycloplegics, or pupillary dilators, which are used in the treatment of diseases of the eye.

The composition described herein may be varied to include at least one ophthalmically acceptable pH adjusting agent and/or buffer, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane, triethanolamine; and buffers such as citrate/dextrose, sodium bicarbonate and ammonium chloride, or an amino acid. Such an acid, base and/or buffer may be included in an amount required to maintain pH of the composition in an ophthalmically acceptable range.

The composition may optionally include at least one, tonicity agent, such as an ophthalmically acceptable salt in an amount required to bring osmolality of the composition into an ophthalmically acceptable range. Exemplary salts include, but are not limited to, the salts having sodium, potassium, magnesium, calcium or ammonium cations and chloride, citrate, ascorbate, borate, phosphate, bicarbonate, sulfate, thiosulfate or bisulfite anions, for example, sodium chloride, potassium chloride, sodium thiosulfate, sodium bisulfite and ammonium sulfate.

In one embodiment, the compositions described herein may comprise an excipient to adjust osmolality. Exemplary excipients include sugars, for example dextrose, lactose, xylitol, mannitol and glycerine.

The compositions described herein may optionally comprise tonicity imparting agents such as; other viscosity imparting agents such as sodium carboxymethylcellulose, microcrystalline cellulose, polyvinylpyrrolidone, polyvinyl alcohol.

In some embodiments, the composition described herein may comprise suitable absorption enhancers, such as surfactants, bile acids; stabilizing agents such as antioxidants, like bisulfites and ascorbates; and/or metal chelating agents, such as sodium edetate; and drug solubility enhancers, such as polyethylene glycols.

In another embodiment of the invention, the ophthalmic compositions described herein may comprise a surfactant such as polyoxyethylene fatty acid glycerides, vegetable oils, e.g., polyoxyethylene (60) hydrogenated castor oil; and polyoxyethylene alkylethers and alkylphenyl ethers, e.g., octoxynol 10, octoxynol 40, a polyoxyethylene fatty acid ester, polyoxyethylene alkylphenyl ether, and polyoxyethylene alkyl ether, or mixtures thereof or a thickening agent such as a carboxyvinyl polymer, polyvinyl polymer, and polyvinylpyrrolidones, as described in U.S. Pat. No. 5,951,971 to Kawashima.

In one embodiment, the compositions described herein may comprise at least one ophthalmically acceptable acid having at least two dissociable hydrogen groups that may be included in a polymer-containing composition as interactive agents to retard the release of the drug through inhibition of erosion of the polymer, as disclosed in International Patent Publication No. WO 95/03784, incorporated herein by reference in its entirety. Other exemplary interactive agents include, but are not limited to, boric, lactic, orthophosphoric, citric, oxalic, succinic, tartaric and formic glycerophosphoric acids.

Examples of ophthalmic solutions and ophthalmic ointments can be formulated into such preparations using methods known to those of ordinary skill in the art. In the case of ophthalmic solutions, for example, they can be prepared using distilled water, an aqueous base, or any other acceptable base; tonicity agents such as sodium chloride and concentrated glycerol; buffers such as sodium phosphate and sodium acetate; surfactants such as polyoxyethylene sorbitan monooleate, stearic polyoxyl 40, and polyoxyethylene hydrogenated castor oil; stabilizers such as sodium citrate and sodium edetate; preservatives such as benzalkonium chloride, thimerosal, chlorobutanol, sodium chloride, boric acid, parahydroxybenzoic acid esters (sorbate, benzoate, propionate), chlorobutanol, benzyl alcohol, mercurials, paraben such as propyl 4-hydroxybenzoate (or propylparaben), methyl-P-Hydroxybenzoate (or methylparaben), and mixtures thereof. In some embodiments, preservatives comprise benzalkonium chloride or thimerosal.

In some embodiments, in the ophthalmic composition of this invention, the ophthalmic carrier may be a sterile aqueous carrier or a salve or ointment carrier. Such salves or ointments typically comprise one or more 4-aminoquinoline compounds dissolved or suspended in a sterile pharmaceutically acceptable salve or ointment base, such as a mineral oil-white petrolatum base. In salve or ointment compositions, anhydrous lanolin may also be included in the formulation. Thimerosal or chlorobutanol may also be added to such ointment compositions as antimicrobial agents.

In yet another embodiment of the invention, the ophthalmic carrier may be olive oil, arachis oil, castor oil, polyoxyethylated castor oil, mineral oil, petroleum jelly, dimethyl sulphoxide, an alcohol, liposome, silicone fluid and mixtures thereof as taught by U.S. Pat. No. 6,254,860, to Garst.

In some embodiments, the composition described herein may comprise an ophthalmically acceptable xanthine derivative such as caffeine, theobromine or theophylline can be included in the composition, substantially as disclosed in U.S. Pat. No. 4,559,343 to Han & Roehrs, incorporated herein by reference in its entirety.

In some embodiments, the compositions described herein may include at least one antioxidant to enhance chemical stability. Exemplary antioxidants include, but are not limited to, ascorbic acid and derivatives, sodium metabisulfite, vitamin E and analogs thereof and butylated hydroxyanisole (BHA).

In one embodiment, the composition described herein may comprise at least one ophthalmic lubricating agents to promote lacrimation. Exemplary lubricants include, but are not limited to, polyvinyl alcohol, methylcellulose, hydroxypropyl methylcellulose, polyvinylpyrrolidone.

In some embodiments, the compositions described herein further comprise a vasoconstrictor. Exemplary vasoconstrictors include, but are not limited to, tetrahydrozoline, ephedrine, naphazoline, phenylephrine, and/or mixtures thereof.

As used herein, any agent used for prevention or treatment of an ocular infection is administered in an amount effective to treat or prevent that infection, namely in an amount and in a dosage regimen effective to prevent, reduce the duration and/or severity of the infection and/or shedding of the infectious agent.

In some embodiments, the compound described herein is in the range of about 0.001% to 30%, or about 0.001% to 20% or about 0.001 to 10% weight of the total composition. In another embodiment, the amount of the compound is in the range of about 0.001 - 5% weight of the total composition.

Different concentrations of compounds described herein may achieve similar results, with the compounds described herein administered, typically and without limitation, from one to ten times daily, including 2, 3, 4, 5, 6, 7, 8, 9 and 10 times daily. The amount (e.g., number of drops of drug product) of the drug product administered to the patient (typically one or two drops per eye per dose when a dropper is used), also may vary depending on the ocular dispenser used to administer the drug product and the concentration of the binding reagent and, where appropriate, anti-inflammatory agent in the drug product. A person of average skill in the pharmaceutical and medical arts will appreciate that it will be a matter of simple design choice and optimization to identify a suitable dosage regimen for treatment of any given ocular infection or prevention of an ocular infection.

Any of the compounds described herein may be formulated into ophthalmic pharmaceutical compositions suitable for topical administration. In some embodiments, the ophthalmically acceptable composition is topically administered. In one embodiment, ophthalmically acceptable composition is topically administered to the cornea and/or conjunctiva of the subject.

The active ingredients can be administered in the conjunctival sack as eye drops, ointments, gels, sustained release carriers, slow dissolving capsules placed in the conjunctival sack, via release from a contact lens, subconjunctivally by injection, or intravitreally by injection, by preparing a suitable formulation of the active ingredient and utilizing procedures well known to those skilled in the art. In one embodiment, the formulations are prepared with suitable nontoxic pharmaceutically acceptable ingredients. These ingredients are known to those skilled in the preparation of eye drops, eye ointments, subconjunctival and intravitreal injections. Some of these ingredients can be found in Remington's Pharmaceutical Sciences, 17th edition, 1985, a standard reference in the field. The choice of suitable carriers may be dependent upon the exact nature of the eye drops, eye ointments, subconjunctival, intravitreal dosage form desired, e.g. solutions, sprays, drops, gels, pastes, patches.

The compounds described herein may be administered via a biocompatible and implantable controlled-release drug delivery device as taught in U.S. Pat. No. 6,331,313, to Wong. The compounds described herein can also be administered in sustained release forms or from sustained release drug delivery systems which can be found in Remington's Pharmaceutical Sciences, 17th edition, 1985, Mack Publishing Company, Easton, Pa., and International Program on Chemical Safety (IPCS).

In one embodiment, the ophthalmic carrier is a conjunctival insert. Preparation of said inserts is taught by U.S. Pat. No. 6,217,896 to Benjamin and other methods are well known in the art.

The ophthalmic compositions described herein may be formulated in any applicable dosage form. Exemplary dosage form include, but are not limited to, eye drops (liquids), ointments, oils, multi-phase systems (such as, liposome, micellular, homogenates or suspensions of liquids or semi-solid or solid particles), gels, creams, pads or strips. In one embodiment, the active ingredient (drug) is in a water-based (aqueous) drug product. In another embodiment, the active ingredient is in a petrolatum-based drug product. One embodiment of the present invention is the use of topical formulations of compounds described herein to treat ocular infections caused by, without limitation, herpes simplex virus, cytomegalovirus, varicella zoster virus, adenovirus and/or a combination thereof.

In one embodiment, a combined dosage form is provided comprising at least one compound described herein in combination with one or more active ingredient, such as, without limitation, an anti-inflammatory agent and/or an antibiotic. The dosage form comprises an ophthalmological carrier which comprises acceptable excipients, such as, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water, as are broadly known in the pharmaceutical arts According to some aspects of the present invention, the pharmaceutical compositions of this invention may be in the form of an orally acceptable dosage form including, but not limited to, capsules, tablets, suspensions or solutions. The oral dosage form may include at least one excipient. Excipients used in oral formulations of the present can include diluents, substances added to mask or counteract a disagreeable taste or odor, flavors, dyes, fragrances, and substances added to improve the appearance of the composition. Some oral dosage forms of the present invention suitably include excipients, such as disintegrants, binding agents, adhesives, wetting agents, polymers, lubricants, or glidants that permit or facilitate formation of a dose unit of the composition into a discrete article such as a capsule or tablet suitable for oral administration. Excipient-containing tablet compositions of the invention can be prepared by any suitable method of pharmacy which includes the step of bringing into association one or more excipients with at least one compound of the present invention in a combination of dissolved, suspended, nanoparticulate, microparticulate or controlled-release, slow-release, programmed-release, timed-release, pulse-release, sustained-release or extended-release forms thereof.

In certain embodiments, the pharmaceutically compositions of this invention are formulated for oral administration. For oral administration to humans, the dosage range is about 0.01 to about 1000 mg/kg body weight in divided doses. In one embodiment the dosage range is about 0.1 to about 100 mg/kg body weight in divided doses. In another embodiment the dosage range is about 0.5 to about 20 mg/kg body weight in divided doses. For oral administration, the compositions may be provided in the form of tablets or capsules containing 1.0 to 1000 milligrams of the active ingredient, particularly, about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

In some embodiments, the pharmaceutical composition of this invention is formulated for intraocular administration, for example, by subconjuctival (into the subconjuctival), intravitreal (into the vitreous), subretinal (under the retina), or retrobulbar (behind the eyeball) injection. The composition includes any carrier or excipients that known to one skilled in the art that are suitable for intraocular administration. Exemplary excipients include those discussed in U.S. Patent Application Publication No. 2008/0241252 to Lyons et al. and PCT Application Publication No. WO 2004/043480, which are incorporated by references in their entireties.

It should also be understood that a specific dosage and treatment regimen for any particular patient will depend upon a variety of factors, including the activity of the specific compound employed, the mode of administration, the age, body weight, general health, gender, diet, rate of excretion, drug combination, and the judgment of the treating physician, the condition being treated and the severity of the condition. Such dosage may be ascertained readily by a person skilled in the art. This dosage regimen may be adjusted to provide the optimal therapeutic response.

The compositions described herein may be sterilized by conventional, well known sterilization techniques, or may be sterile filtered. The resulting aqueous solutions may be packaged for use as is, or lyophilized, the lyophilized preparation being combined with a sterile solution prior to administration.

Compounds of the present invention may optionally be administered in conjunction with other active compounds and/or agents useful in the treatment of viral infections as described herein. The other compounds may optionally be administered concurrently. As used herein, the word "concurrently" means sufficiently close in time to produce a combined effect (that is, concurrently may be simultaneously, or it may be two or more events occurring within a short time period before or after each other).

D. Methods of Use

One aspect of the invention is to provide methods for treating or preventing a viral infection of the eye. In some embodiments, the methods comprise administering a pharmaceutically acceptable composition to the ocular region of a subject. For example, the composition may be topically applied (e.g. as eye drops) to the eye. The pharmaceutically acceptable composition comprises a pharmaceutically acceptable carrier and at least one compound described herein. In another embodiment, the pharmaceutical composition may be orally administered to the subject.

The viral infection described herein may be any applicable virus that can infect the eye. Exemplary viral infections include, but are not limited to, influenza, herpes simplex virus (HSV), human herpes virus, cytomegalovirus (CMV), Epstein-Barr virus (EBV), varicella zoster virus (VZV), orthopox virus, variola major and minor, vaccinia, cowpox, camelpox, monkeypox, papilloma virus, adenovirus, polyoma virus including JC virus, BK virus, SV40 and a combination thereof. In some embodiments, at least one viral infection is selected from cytomegalovirus, varicella zoster virus, adenovirus, herpes simplex virus and Epstein-Barr virus. In another embodiment, the viral infection is a topical viral infection.

Another aspect of the invention is to provide methods for treatment or preventing a posterior ocular condition. In some embodiments, posterior ocular condition or degeneration condition of retina or retinal nerve, is selected from macular degeneration, retinopathy, or retinitis pigmentosa. Further, in one embodiment, the pharmaceutical composition for treating posterior ocular condition is intraocular administered (for example, intraocular injection including retrobulbar, intravitreal, intraretinal or subconjctival injection).

A condition of the posterior segment (posterior ocular condition) of the eye is a disease, ailment or condition which significantly affects or involves a tissue or cell type in a posterior ocular region or site (that is, in a position posterior to a plane through the posterior wall of the lens capsule), such as the accordingly located parts of the choroid or sclera, vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age-related macular degeneration and exudative age-related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection). The infiltrative growth of new blood vessels can disrupt or destroy nervous tissue; thus the inhibition of angiogenesis can also be considered to provide protection to affected neurons.

E. Examples

Evaluation of the biological activity of the compounds described herein may be accomplished through in vitro, ex vivo, and in vivo assays that are well known to one skilled in the art.

Example I

Evaluation Antiviral Activity

The antiviral activity of the compounds described herein is described in U.S. Pat. Nos. 6,716,825, 7,034,014, 7,094,772, 7,098,197, and 7,452,898, which are incorporated by reference in their entireties. For example, exemplary biological assays and the antiviral activity and selectivity of exemplary compounds against human cytomegalovirs (HCMV), poxvirus, herpes virus are described in Examples 17 to 21 of U.S. Pat. No. 6,716,825. Furthermore, more exemplary biological assays are discussed in Kern et al., AAC 46 (4):991; Williams-Aziz et al., AAC 49(9):3724; Beadle et al., AAC 46 (8): 2381 and Hostetler et al., Antiviral Research, 82, A84-A98 (2009).

The antiviral activities of CMX001 and cidofovir against several viruses are summarized in Table 1 below.

TABLE 1

CMX001 has enhanced in vitro potency against dsDNA viruses.

| Virus | Cidofovir EC50 (µM) | CMX001 EC50 (µM) | Enhanced Activity |
|---|---|---|---|
| Adenovirus | 1.3 | 0.02 | 65 |
| BK Virus | 115 | 0.13 | 885 |
| CMV | 0.4 | 0.001 | 400 |
| EBV | >108 | 0.04 | >2700 |
| HHV-6 | 5.4 | 0.007 | 771 |
| HPV 11 | 716 | 17 | 42 |
| HSV-1 | 5.5 | 0.06 | 92 |
| Vaccinia Virus | 46 | 0.8 | 57 |
| Variola major | 27.3 | 0.1 | 271 |
| VZV | 0.5 | 0.004 | 125 |

The antiviral activities of the exemplary compounds of the present invention are also discussed in Kern et al., AAC 46 (4):991; Williams-Aziz et al., AAC 49(9):3724; and Beadle et al., AAC 46 (8): 2381 and Hostetler et al., Antiviral Research, 82, A84-A98 (2009), which are incorporated by references in their entireties. For example, Tables 2-5 of Kern et al. describe the anti-viral activities of HDP-CDV, ODE-CDV, HDP-cCDV, ODE c-CDV, etc. against vaccinia virus (VV) and cowpox virus (CV). Tables 1-6 of Beadle et al. describe antiviral activities of ODE-CDV, HDP-CDV, ODP-CDV, etc. against cytomegalovirus (CMV) and herpes simplex viruses (HSV). Tables 2-7 of Williams-Aziz et al. describe the antiviral activities and toxicities of several exemplary compounds against varicella-zoster virus (VZV), HSV, CMV, human herpes viruses (HHV), Epstein-Barr virus (EBV), etc. Tables 1-5 of Hostetler et al, describe antiviral activities of exemplary compounds against poxviruses, herpes viruses, adenoviruses, polyoma viruses, herpes viruses, HCMV, Orf virus, VV, etc.

Example II

Irritation Test of the Ophthalmic Composition of CMX001

A study is conducted to assess irritation and/or corrosion produced by a single exposure of 5% CMX001 gel to the eye of albino rabbits. The formulation of the CM001 gel is shown below in Table 2.

TABLE 2

Ophthalmic formulation of CMX001
Chemicals/Raw Materials

| Chemical Name | Part # | Provider | % w/w | Qty | UOM |
|---|---|---|---|---|---|
| Purified Water USP | 158560 | DPT | 73.2500 | 0.7000 | L |
| Carbomer 934P | 151380 | DPT | 1.0000 | 0.0100 | kg |
| Trolamine | 156120 | DPT | 0.5000 | 5.0000 | g |
| Propylparaben | 155530 | DPT | 0.0500 | 0.5000 | g |
| Methylparaben | 154300 | DPT | 0.2000 | 2.0000 | g |
| Propylene Glycol | 155510 | DPT | 10.0000 | 0.1000 | kg |
| Glycerin (99%) USP | 154640 | DPT | 10.0000 | 0.1000 | kg |
| CMX001 | RD161260 | Client | 5.0000 | 0.0500 | kg |

Three male Hra:(NZW)SPF rabbits received approximately 0.1 mL (0.1 g) of 5% CMX001 in the everted lower lid of the right eye with the left eye serving as control. The animals are evaluated for obvious pain upon instillation. Approximately 24 hours post-dose, the treated eyes are washed using room-temperature physiological saline. Eye irritation is evaluated and scored on a scale of 1 (least severe) to 4 (most severe) using the Draize technique at approximately 1, 24, 48, and 72 hours after instillation. The highest possible score using this method is 120. Since all animals are normal at the 72-hour scoring, the study is terminated per protocol. Mortality, clinical observations, and body weights are also assessed.

All rabbits survived to study termination. All animals appeared normal at the time of clinical observations and body weights are unremarkable. There is no indication of pain in any animal upon instillation of 5% CMX001 gel or shortly thereafter. At 1 hour postinstillation, all three animals had findings in the conjunctivae for redness (one animal with Score 2 and two animals with Score 1) and chemosis (three animals with Score 1). At 24 hours postinstillation, all animals had negative fluorescein stain examination. Two animals had conjunctival redness (Score 1) and chemosis (Score 1) at 24 hours postinstillation. All animals are normal at the 48 and 72 hour postinstillation scoring intervals. The maximum mean primary irritation score was 4.7 at 1 hour postinstillation. There was no evidence of corrosion at any time during the study. Therefore, 5% CMX001 Gel is concluded to be minimally irritating and non-corrosive when administered as a single ocular dose to rabbits.

Example III

Animal Model to Evaluate the Efficacy of Ophthalmic Application of Compounds Described Herein The compounds described in the present invention may be tested in any animal model known to those skilled in the art. Exemplary animal models include, but are not limited to, cats, rabbit, and rat. An exemplary animal model is described below:

Testing cats are randomly assigned to either a treatment or control group. Ocular infection with a selected virus is induced on day 0 in all cats via inoculation of both eyes with an appropriate composition containing the selected virus. After the selected virus is inoculated, the treatment group received ophthalmic composition of compounds described herein in appropriate ophthalmic carrier in both eyes, and the control group received merely the ophthalmic carrier in both eyes. A standardized scoring method is used to evaluate clinical signs of the selected virus infection in each cat once daily for 24 days. The amount of ocular viral shedding is assessed by use of a quantitative real-time PCR procedure every 3 days during the study period. Clinical scores and viral quantification will be averaged over the pretreatment, treatment, and post-treatment periods for each cat. It is expected that clinical scores and amount of viral ocular shedding will be significantly lower in the treatment group, compared with findings in the control group.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An ophthalmic composition comprising: an ophthalmically acceptable carrier and a compound in an amount effective to treat a viral infection, wherein said compound is

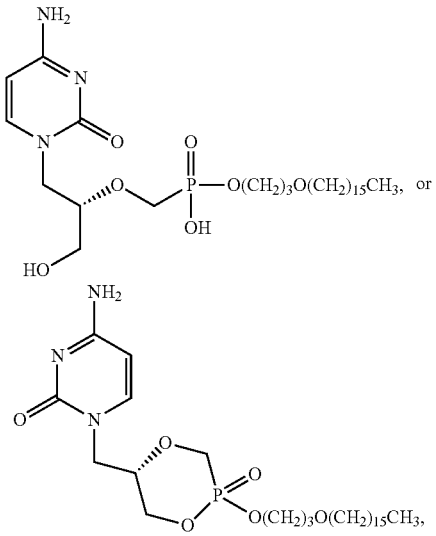

or a pharmaceutically acceptable salt thereof.

2. The composition of claim 1, wherein the compound is

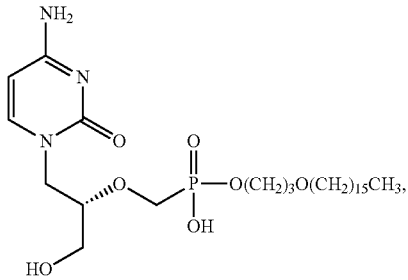

or a pharmaceutically acceptable salt thereof.

3. The composition of claim 1, wherein the compound is

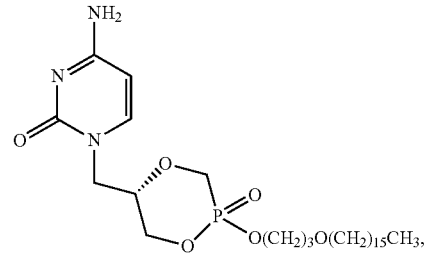

or a pharmaceutically acceptable salt thereof.

4. The composition of claim 1, wherein the composition comprises a topically acceptable carrier.

5. The composition of claim 1, wherein the ophthalmic composition is in the form selected from the group consisting of an aqueous solution, a non-aqueous solution, a suspension, a solution/suspension, a gel, a cream, an ointment, and an emulsion.

6. The composition of claim 1, wherein the composition further comprises at least one excipient selected from the group consisting of stabilizer, a penetrating enhancer, a pH adjusting agent, an antimicrobial preservative, a lubricant, a viscosifier, and a wetting agent.

7. The composition of claim 1, further comprises purified water, carbomer, trolamine, propylparaben, methylparaben, propylene glycol, and glycerin.

8. The composition of claim 1, wherein the amount of the compound is in the range of about 0.001% to 30% by weight.

9. The composition of claim 8, wherein the amount of the compound is about 5% by weight.

10. A method of treating a viral infection of the eye comprising administering an ophthalmic composition to a subject, wherein the composition comprises an ophthalmically acceptable carrier and

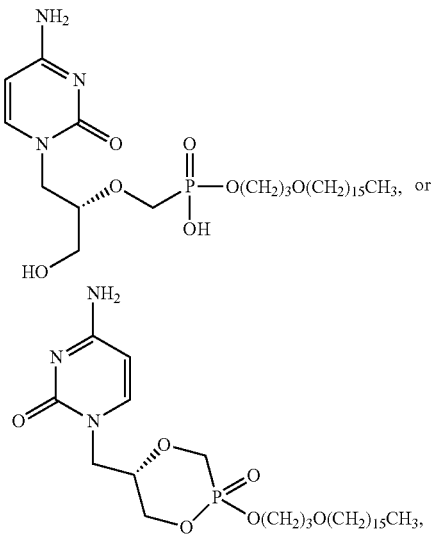

or a pharmaceutically acceptable salt thereof.

11. The method of claim 10, wherein the compound is

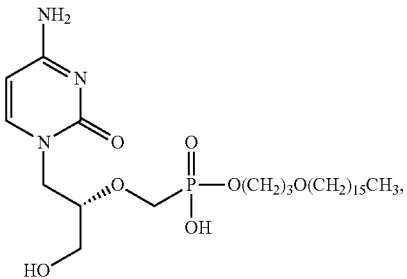

or a pharmaceutically acceptable salt thereof.

12. The method of claim 10, wherein the compound is

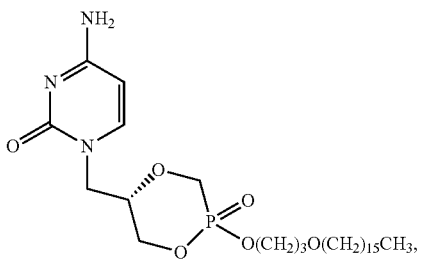

or a pharmaceutically acceptable salt thereof.

13. The method of claim 10, wherein said viral infection is selected from the group consisting of influenza, herpes simplex virus (HSV), human herpes virus, cytomegalovirus (CMV), Epstein-Barr virus (EBV), varicella zoster virus (VZV), orthopox virus, variola major and minor, vaccinia, cowpox, camelpox, monkeypox, papilloma virus, adenovirus, polyoma virus including JC virus, BK virus, SV40 and a combination thereof.

14. The method of claim 13, wherein said viral infection is selected from the groups consisting of cytomegalovirus, varicella zoster virus, adenovirus, herpes simplex virus and Epstein-Barr virus.

15. The method of claim 10, wherein the composition is topically administered to the eye.

16. The method of claim 15, wherein the composition is topically administered to the cornea and/or conjunctiva of the subject.

17. The method of claim 10, wherein the composition is intraocularly administered.

18. The method of claim 17, wherein the composition is administered by intraocular injection.

19. The method of claim 18, wherein the composition is administered by retrobulbar, intravitreal, intraretinal or subconjunctival injection.

20. The method of claim 10, wherein the viral infection is due to a double stranded DNA (dsDNA) virus.

* * * * *

UNITED STATES PATENT AND TRADEMARK OFFICE
CERTIFICATE OF CORRECTION

PATENT NO.       : 8,614,200 B2                                    Page 1 of 1
APPLICATION NO. : 13/386604
DATED            : December 24, 2013
INVENTOR(S)      : Painter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 55 days.

Signed and Sealed this
Twenty-second Day of September, 2015

Michelle K. Lee
*Director of the United States Patent and Trademark Office*